(12) United States Patent
Alcouffe et al.

(10) Patent No.: US 7,553,845 B2
(45) Date of Patent: Jun. 30, 2009

(54) SUBSTITUTED INDOLIZINE 1,2,3,6,7,8 DERIVATIVES, FGFS INHIBITORS, A METHOD FOR THE PREPARATION THEREOF AND PHARMACEUTICAL COMPOSITIONS CONTAINING SAID DERIVATIVES

(75) Inventors: Chantal Alcouffe, Roquettes (FR); Alain Badorc, Roquettes (FR); Francoise Bono, Toulouse (FR); Marie-Francoise Bordes, Toulouse (FR); Nathalie Guillo, Toulouse (FR); Jean-Marc Herbert, Tournefeuille (FR)

(73) Assignee: sanofi-aventis, Paris (FR)

( * ) Notice: Subject to any disclaimer, the term of this patent is extended or adjusted under 35 U.S.C. 154(b) by 105 days.

(21) Appl. No.: 11/378,972

(22) Filed: Mar. 17, 2006

(65) Prior Publication Data

US 2006/0199962 A1    Sep. 7, 2006

Related U.S. Application Data

(63) Continuation of application No. PCT/FR2004/002347, filed on Sep. 16, 2004.

(30) Foreign Application Priority Data

Sep. 18, 2003  (FR) .................................. 03 10957

(51) Int. Cl.
*A61K 31/437*    (2006.01)
*C07D 471/04*    (2006.01)

(52) U.S. Cl. ...................................... 514/299; 546/112
(58) Field of Classification Search ................. 546/112; 514/299
See application file for complete search history.

(56) References Cited

U.S. PATENT DOCUMENTS

| 4,378,362 A | 3/1983 | Rosseels et al. |
|---|---|---|
| 4,400,387 A | 8/1983 | Rosseels et al. |
| 4,499,095 A | 2/1985 | Rosseels et al. |
| 7,442,708 B2 * | 10/2008 | Badore et al. ............... 514/299 |
| 2003/0119793 A1 | 6/2003 | Ledford et al. |
| 2005/0203126 A1 | 9/2005 | Badorc et al. |

FOREIGN PATENT DOCUMENTS

WO     03/084956     * 10/2003

OTHER PUBLICATIONS

Chen et al., "FGFR1/Pi3K/AKT, etc.," Journal of Cellular Biochemistry 101: 1492-1504 (2007).*
Cao, "Antiangiogenic cancer therapy", Seminars in Cancer Biology 14 (2004) 139-145.*
Sathornsumette et al., "Antiangiogenic Therapy, etc.," Current Pharmaceutical Design, 2007, 13, 3545-3558.*
Kwabi-Addo et al., "The role of fibroblast, etc.," Endocrine-Related Cancer (2004) 11 709-724.*
Rosseels, et al., Study in the Indolizines Series. V. Effect of Indolizine Substitution i Position 1 in the Butoprozine Series, European J. of Med. Chemistry; 1983; 18(4); pp. 339-346.
Compounds for Screening, SPECS and bioSPECS XP002224380, Database Chemcats chemical abstracts service, Columbus, Ohio; Jul. 1, 2001.

* cited by examiner

*Primary Examiner*—Patricia L Morris
(74) *Attorney, Agent, or Firm*—Ronald G. Ort; Paul Darkes

(57) ABSTRACT

The invention is directed to a compound of formula I,

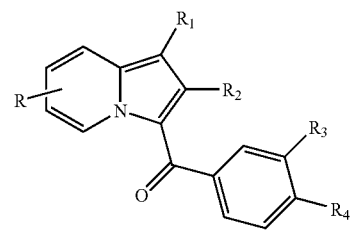

wherein R, $R_1$, $R_2$, $R_3$ and $R_4$ are as defined herein, or a pharmaceutically acceptable salt thereof, and its pharmaceutically composition, preparation and uses as an inhibitor of FGFs (fibroblast growth factors).

10 Claims, No Drawings

SUBSTITUTED INDOLIZINE 1,2,3,6,7,8 DERIVATIVES, FGFS INHIBITORS, A METHOD FOR THE PREPARATION THEREOF AND PHARMACEUTICAL COMPOSITIONS CONTAINING SAID DERIVATIVES

This application is a continuation of International Application No. PCT/FR2004/002347, filed Sep. 16, 2004.

FIELD OF THE INVENTION

The subject of the present invention is novel 1,2,3,6,7,8-substituted indolizine derivatives, which are inhibitors of FGFs (fibroblast growth factors), the method for preparing them and the pharmaceutical compositions containing them.

BACKGROUND OF THE INVENTION

FGFs are a family of polypeptides which are synthesized by a large number of cells during embryonic development and by cells of adult tissues under various pathological conditions Some derivatives of naphthyridinediamines and corresponding ureas are known which are selective inhibitors of FGF-1 (Batley B. et al., *Life Sciences*, (1998), Vol. 62 No. 2, pp. 143-150; Thompson A. et al., *J. Med. Chem.*, (2000), Vol. 43, pp. 4200-4211).

Some indolizine derivatives are described in Patent Applications and Patents U.S. Pat. No. 4,378,362, FR 2 341 578, GB 2 064 536, EP 0 097 636, EP 302 792, EP 0 382 628, and EP 0 235 111. These compounds are useful in the treatment of angina pectoris and arrhythmia. Calcium translocation inhibiting properties are described for some of these compounds.

Patent Application EP 0 022 762 also describes some indolizine derivatives which possess a xanthine oxidase and adenosine deaminase inhibiting activity and a uricosuric activity. These compounds may be used in the treatment of physiological disorders which occur following an excess of uric acid, disruptions of the immune system and as parasitic agents.

It has now been found that some compounds, derived from indolizine, are potent antagonists of the binding of FGFs to their receptors.

SUMMARY OF THE INVENTION

Accordingly, the subject of the present invention is novel indolizine derivatives of formula I,

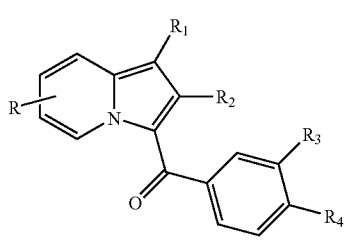

(I)

in which:

R at the 6-, 7- or 8-positions of the indolizine represents a hydrogen atom, a halogen atom, a methyl radical, a hydroxyl radical, a linear or branched alkoxy radical of 1 to 5 carbon atoms, a carboxyl radical, an alkoxycarbonyl radical of 2 to 6 carbon atoms or a radical of formula:

—$NR_5R_6$
—NH—$SO_2$-Alk
—NH—CO-Alk
—NH—$CO_2$-Alk
—O-Alk-$COOR_7$
—O-Alk-$NR_5R_6$
—O—$(CH_2)_n$—Ph
—CO—$NR_5R_6$ where
Alk represents an alkyl radical or a linear or branched alkylene radical of 1 to 5 carbon atoms,
n represents an integer from 0 to 5,
$R_5$ and $R_6$, which are identical or different, each represent a hydrogen atom, a linear or branched alkyl radical of 1 to 5 carbon atoms or a benzyl radical,
$R_7$ represents a hydrogen atom or an alkyl radical of 1 to 5 carbon atoms,
Ph represents a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms, $R_1$ represents
a linear or branched alkoxy radical of 1 to 5 carbon atoms,
a carboxyl radical,
an alkoxycarbonyl radical of 2 to 6 carbon atoms,
a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
a 5-membered heteroaryl radical containing a heteroatom chosen from a sulfur atom, an oxygen atom or a nitrogen atom, optionally containing a second nitrogen atom and being optionally substituted with one or more halogen atoms, with one or more linear or branched alkyl radicals of 1 to 5 carbon atoms, with one or more alkoxy radicals of 1 to 5 carbon atoms, with one or more carboxyl radicals or with one or more alkoxycarbonyl radicals of 2 to 6 carbon atoms,
or a 6-membered heteroaryl radical containing 1 or 2 nitrogen atoms and which may be optionally substituted with one or more halogen atoms, with one or more linear or branched alkyl radicals of 1 to 5 carbon atoms, with one or more alkoxy radicals of 1 to 5 carbon atoms, with one or more carboxyl radicals or with one or more alkoxycarbonyl radicals of 2 to 6 carbon atoms, $R_2$ represents an alkyl radical of 1 to 5 carbon atoms, a cycloalkyl radical of 3 to 6 carbon atoms or a phenyl radical which is optionally substituted with one or more halogen atoms, with one or more alkoxy radicals of 1 to 5 carbon atoms, $R_3$ and $R_4$, which are identical or different, each represent a hydroxyl radical, an alkoxy radical of 1 to 5 carbon atoms, an amino radical, a carboxyl radical, an alkoxycarbonyl radical of 2 to 6 carbon atoms, a nitro radical, or a radical of formula:

—$NR_5R_6$
—NH—CO-Alk
—NH—CO—$CF_3$
—CO—$NR_5R_6$
—CO—NHOH where
Alk, $R_5$ and $R_6$ have the meaning given above for R, provided, however, that when R represents a hydrogen atom, $R_1$ does not represent a linear or branched alkoxy radical of 1 to 5 carbon atoms, a carboxyl radical, or an alkoxycarbonyl radical of 2 to 6 carbon atoms, except in the case where $R_3$ or $R_4$ represents a radical —CO—$NR_5R_6$ or a radical —CO—NHOH, optionally in the form of one of their pharmaceutically acceptable salts.

DETAILED DESCRIPTION OF THE INVENTION

A particular embodiment of the invention is a compound of formula I in which:

R at the 6-, 7- or 8-positions of the indolizine represents a hydrogen atom, a halogen atom, a hydroxyl radical, a linear or branched alkoxy radical of 1 to 5 carbon atoms, a carboxyl radical, an alkoxycarbonyl radical of 2 to 6 carbon atoms or a radical of formula:
—$NR_5R_6$
—NH—$SO_2$-Alk
—NH—CO-Alk
—NH—$CO_2$-Alk
—O-Alk-$COOR_7$
—O-Alk-$NR_5R_6$
—CO—$NR_5R_6$
where
Alk represents an alkyl radical or a linear or branched alkylene radical of 1 to 5 carbon atoms,
$R_5$ and $R_6$, which are identical or different, each represent a hydrogen atom, a linear or branched alkyl radical of 1 to 5 carbon atoms or a benzyl radical,
$R_7$ represents a hydrogen atom or an alkyl radical of 1 to 5 carbon atoms, $R_1$ represents
a linear or branched alkoxy radical of 1 to 5 carbon atoms,
a carboxyl radical,
an alkoxycarbonyl radical of 2 to 6 carbon atoms,
a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
a 5-membered heteroaryl radical containing a heteroatom chosen from a sulfur atom, an oxygen atom or a nitrogen atom, optionally containing a second nitrogen atom and being optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
or a 6-membered heteroaryl radical containing 1 or 2 nitrogen atoms and which may be optionally substituted with one or more halogen atoms, with one or more alkoxy radicals of 1 to 5 carbon atoms, with one or more carboxyl radicals or with one or more alkoxycarbonyl radicals of 2 to 6 carbon atoms, $R_2$ represents an alkyl radical of 1 to 5 carbon atoms, a cycloalkyl radical of 3 to 6 carbon atoms or a phenyl radical which is optionally substituted with one or more halogen atoms, with one or more alkoxy radicals of 1 to 5 carbon atoms, $R_3$ and $R_4$, which are identical or different, each represent a hydroxyl radical, an alkoxy radical of 1 to 5 carbon atoms, an amino radical, a carboxyl radical, an alkoxycarbonyl radical of 2 to 6 carbon atoms, a nitro radical, or a radical of formula:
—$NR_5R_6$
—NH—CO-Alk
—CO—$NR_5R_6$
—CO—NHOH
where
Alk, $R_5$ and $R_6$ have the meaning given above for R, provided, however, that when R represents a hydrogen atom, $R_1$ does not represent a linear or branched alkoxy radical of 1 to 5 carbon atoms, a carboxyl radical, or an alkoxycarbonyl radical of 2 to 6 carbon atoms, except in the case where $R_3$ or $R_4$ represents a radical —CO—$NR_5R_6$ or a radical —CO—NHOH, optionally in the form of one of their pharmaceutically acceptable salts.

A particular embodiment of the invention is a compound of formula I in which:

R at the 6-, 7- or 8-positions of the indolizine represents a hydrogen atom, a linear or branched alkoxy radical of 1 to 5 carbon atoms, an alkoxycarbonyl radical of 2 to 6 carbon atoms or a radical of formula:
—$NR_5R_6$
—CO—$NR_5R_6$
where
$R_5$ and $R_6$ are identical or different and each represent a hydrogen atom, a linear or branched alkyl radical of 1 to 5 carbon atoms or a benzyl radical, $R_1$ represents
a linear or branched alkoxy radical of 1 to 5 carbon atoms,
a carboxyl radical,
a phenyl radical which is optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
a 5-membered heteroaryl radical containing a heteroatom chosen from a sulfur atom, an oxygen atom or a nitrogen atom, optionally substituted with one or more halogen atoms, with one or more alkoxy radicals of 1 to 5 carbon atoms, with one or more carboxyl radicals or with one or more alkoxycarbonyl radicals of 2 to 6 carbon atoms,
or a 6-membered heteroaryl radical containing 1 or 2 nitrogen atoms and which may be optionally substituted with one or more halogen atoms, with one or more alkoxy radicals of 1 to 5 carbon atoms, with one or more carboxyl radicals or with one or more alkoxycarbonyl radicals of 2 to 6 carbon atoms, $R_2$ represents an alkyl radical of 1 to 5 carbon atoms, $R_3$ and $R_4$, which are identical or different, each represents an alkoxy radical of 1 to 5 carbon atoms, an amino radical, a carboxyl radical, a hydroxyl radical, or a radical of formula CO—$NR_5R_6$ where $R_5$ and $R_6$ have the meaning given above for R provided, however, that when R represents a hydrogen atom, $R_1$ does not represent a linear or branched alkoxy radical of 1 to 5 carbon atoms, or a carboxyl radical, except in the case where $R_3$ or $R_4$ represents a radical —CO—$NR_5R_6$, optionally in the form of one of their pharmaceutically acceptable salts.

Particular compounds of the invention are the following:
[3-(4-amino-3-methoxybenzoyl)-6-methoxy-2-methylindolizin-1-yl]carboxylic acid
(4-amino-3-methoxyphenyl)[1-(4-methoxyphenyl)-2-methylindolizin-3-yl]methanone
3-(4-amino-3-methoxybenzoyl)-(1-methoxy-N,2-dimethylindolizin-6-yl)carboxamide
[3-(4-amino-3-methoxybenzoyl)-2-methyl-7-(methylamino)indolizin-1-yl]carboxylic acid
[3-(4-amino-3-methoxybenzoyl)-7-(dimethylamino)-2-methylindolizin-1-yl]carboxylic acid
2-amino-5-({1-methoxy-2-methyl-6-[(methylamino)carbonyl]indolizin-3-yl}-carbonyl)benzoic acid
2-amino-5-[(1,6-dimethoxy-2-methylindolizin-3-yl)carbonyl]benzoic acid
2-amino-5-[(1-methoxy-2-methylindolizin-3-yl)carbonyl]benzamide
[3-(4-amino-3-methoxybenzoyl)-1-(4-methoxyphenyl)-2-methylindolizin-6-yl]carboxamide
2-amino-5-{[2-methyl-1-(2-thienyl)indolizin-3-yl]carbonyl}benzoic acid
(4-amino-3-methoxyphenyl)[2-methyl-1-(2-thienyl)indolizin-3-yl]methanone optionally in the form of one of its pharmaceutically acceptable salts.

The present invention also relates to a method for preparing the compounds of formula I, characterized in that A) an indolizine derivative of formula II,

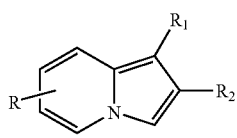
(II)

in which R, $R_1$ and $R_2$ have the meaning given for formula I, but when $R_1$ represents an alkoxycarbonyl radical, R does not represent at the 7-position a radical —$NR_5R_6$, a radical —NH—CO-Alk, a radical —NH—$CO_2$-Alk or a radical —NH—$SO_2$-Alk, is condensed with a derivative of formula III:

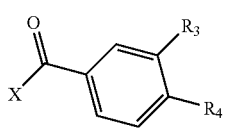
(III)

in which X represents a halogen atom and $R_3$ or $R_4$ represents indistinguishably an alkoxy radical of 1 to 5 carbon atoms, a nitro radical, or an alkoxycarbonyl radical of 2 to 6 carbon atoms or a trifluoroacetamido radical, in order to obtain the compounds of formula Ia, Ib or Ic:

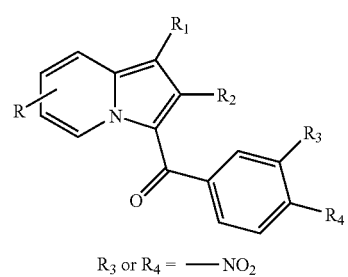
(Ia)

$R_3$ or $R_4$ = —$NO_2$

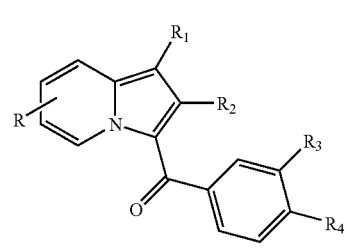
(Ib)

$R_3$ or $R_4$ = —$CO_2$Alkyl

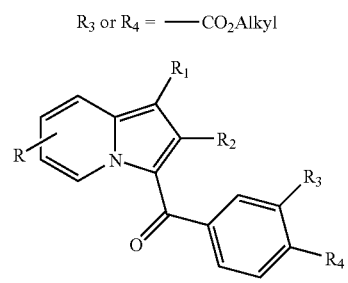
(Ic)

$R_3$ or $R_4$ = —NH—$COCF_3$ and then,
a) the compounds of formula Ia are subjected to a reduction in order to obtain the compounds of formula Id:

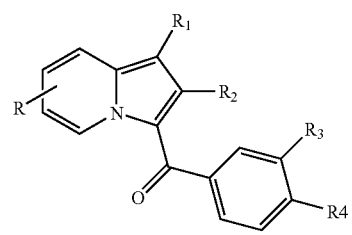
(Id)

$R_3$ or $R_4$ = —$NH_2$ in which $R_3$ or $R_4$ represents an amino radical,
which then compounds of formula Id,
are subjected, when R does not represent a hydroxyl radical, to the action of an alkyl halide in order to obtain the compounds of formula If for which $R_4$ or $R_3$ represents a radical —$NR_5R_6$ (in which $R_5$ represents a hydrogen atom and $R_6$ represents an alkyl radical of 1 to 5 carbon atoms)
or
are subjected, when R does not represent a hydroxyl radical, to an acylation in order to obtain the compounds of formula If for which $R_4$ or $R_3$ represents a radical —NH—CO-Alk, or
b) the compounds of formula Ib in which R and/or R₃ and/or R₄ represent an alkoxycarbonyl radical, are subjected to a saponification in order to obtain the compounds of formula Ie in which R and/or R₃ and/or R₄ represents a carboxyl radical, or
c) when R represents a benzyloxy radical, the compounds of formula Ia are subjected to a catalytic hydrogenation under pressure, in order to obtain the compounds of formula Ig:

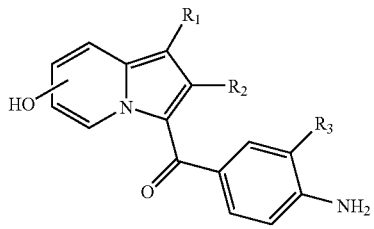

(Ig)

and then these compounds of formula Ig are subjected to a selective O-alkylation in order to obtain the compounds of formula Ih:

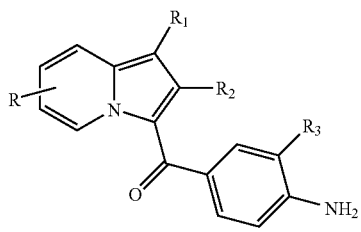

(Ih)

or R represents an alkoxy radical or a radical of formula —O-Alk-COOR₇ which can optionally be saponified in order to obtain a radical of formula —O-Alk-COOH, or
d) when R represents a hydroxyl radical, the compounds of formula Ia are subjected to an O-alkylation, in order to obtain the compounds of formula Ii:

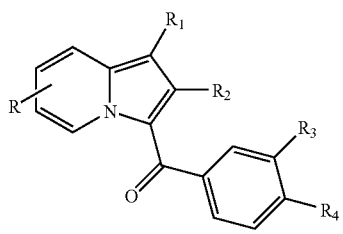

(Ii)

in which R₃ or R₄ have the meanings given for Ia, and R represents an alkoxy radical, a radical of formula —O-Alk-NR₅R₆, or a radical of formula —O-Alk-COOR₇, which can subsequently optionally be saponified in order to obtain a radical of formula —O-Alk-COOH, or
e) when R₁ represents an alkoxycarbonyl radical, the compounds of formula I are subjected to a saponification in order to obtain the compounds of formula Ij:

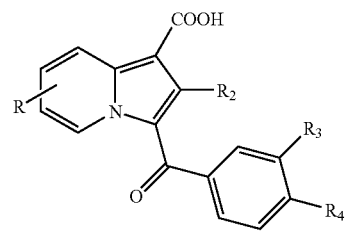

(Ij)

in which R₃ or R₄ have the meanings given above, or
f) when R₁ represents a hydrogen, the compounds of formula I are subjected to a bromination in order to obtain the compounds of formula Ik:

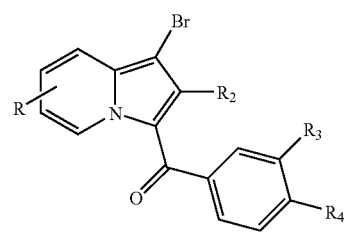

(Ik)

which compounds are then subjected, when R does not represent a halogen such as bromine or iodine, to a coupling with phenylboronic or heteroarylboronic derivatives according to the conditions of the SUZUKI reaction described in *Synth. Commun.*; (1981), *vol* 11, p 513 in order to obtain the compounds of formula Il:

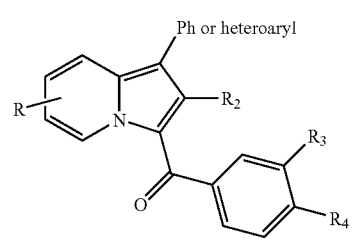

(Il)

in which R does not represent a halogen atom such as bromine or iodine and R₂ and R₃ or R₄ have the meanings given above and R₁ represents a substituted phenyl radical or an optionally substituted 5- or 6-membered heteroaryl, or
g) when R does not represent a hydroxyl or amino or carboxyl radical and R₃ or R₄ represents a carboxyl functional group, the compounds of formula Ie are subjected to a coupling, after activation of the carboxyl functional group, with an amine of formula HNR₅R₆ or of hydroxylamine in order to obtain the compounds of formula Ip:

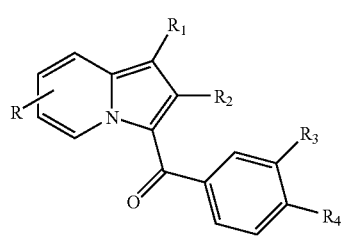
(Ip)

in which $R_3$ or $R_4$ represents a radical —CO—NR$_5$R$_6$ or —CO—NHOH, or

B) when $R_1$ represents an electron-attracting group and R represents a radical 7-NH—CO$_2$-Alk, the pyridines of formula IV:

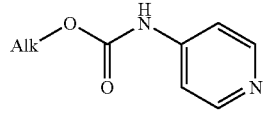
(IV)

are reacted with a bromoacetophenone of formula V:

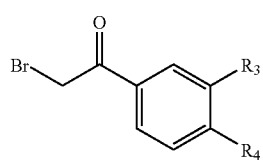
(V)

in order to obtain the compounds of formula VI:

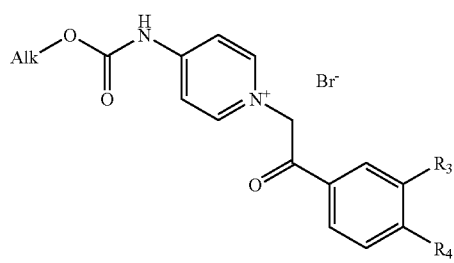
(VI)

which are then subjected to a 1,3-dipolar cycloaddition with benzyl acrylate in the presence of an oxidizing agent in order to obtain the compounds of formula Ia in which $R_1$ represents a benzyloxycarbonyl radical and R represents a radical of formula —NH—COO-Alk at the 7-position, or C) when R represents a radical —NH—CO$_2$tButyl, the compounds of formula Ia are subjected
either to an alkylation followed by a deprotection and an optional second alkylation in order to obtain the compounds of formula Im:

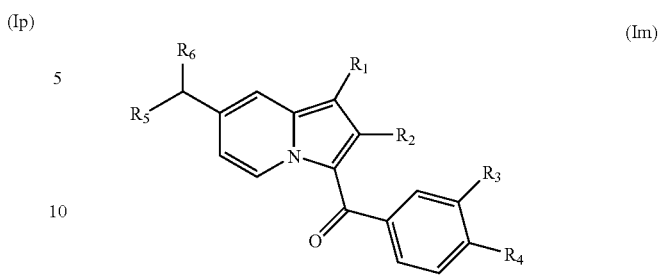
(Im)

or to a deprotection followed by an acylation in order to obtain the compounds of formula In:

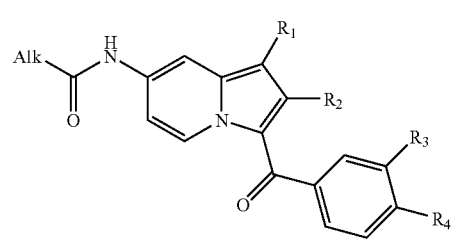
(In)

or to a deprotection followed by a sulfonylation in order to obtain the compounds of formula Io:

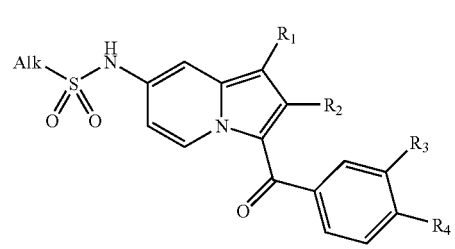
(Io)

Schemes 1, 2 and 3 give the diagrams for the synthesis of products Ia to II and Ip.

SCHEME 1
General Synthesis Diagram

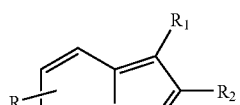

COMPOUNDS (II)

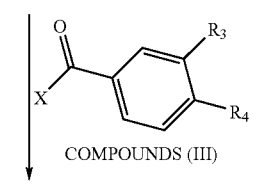

COMPOUNDS (III)

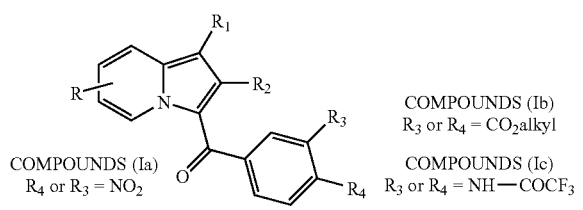

COMPOUNDS (Ia)
R₄ or R₃ = NO₂

COMPOUNDS (Ib)
R₃ or R₄ = CO₂alkyl

COMPOUNDS (Ic)
R₃ or R₄ = NH—COCF₃

REDUCTION / SAPONIFICATION

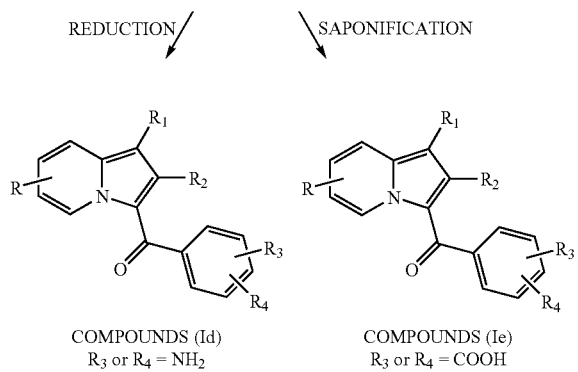

COMPOUNDS (Id)
R₃ or R₄ = NH₂

COMPOUNDS (Ie)
R₃ or R₄ = COOH

ALKYLATION or ACYLATION
R = / = OH

COUPLING

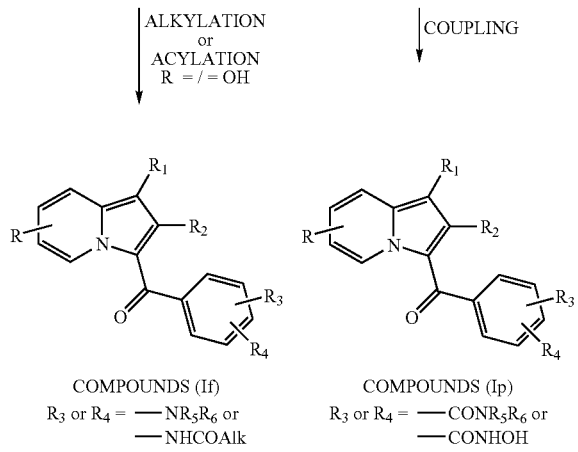

COMPOUNDS (If)
R₃ or R₄ = —NR₅R₆ or
—NHCOAlk

COMPOUNDS (Ip)
R₃ or R₄ = —CONR₅R₆ or
—CONHOH

SCHEME 2

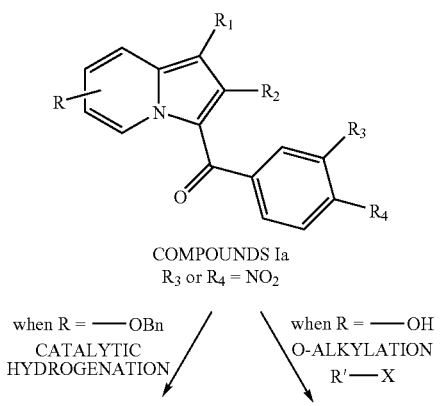

COMPOUNDS Ia
R₃ or R₄ = NO₂ when R = —OBn
CATALYTIC HYDROGENATION when R = —OH
O-ALKYLATION
R'—X

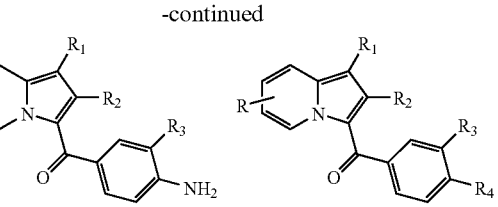

COMPOUNDS Ig
R = —OH

COMPOUNDS Ii
R₃ or R₄ = NO₂
R = —O-Alk,
—O-Alk-COOR₇,
—O-Alk-NR₅R₆

R'—X  SELECTIVE O-ALKYLATION

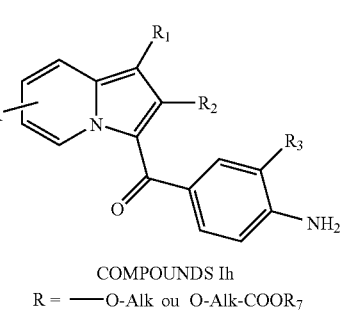

COMPOUNDS Ih
R = —O-Alk ou O-Alk-COOR₇

SCHEME 3

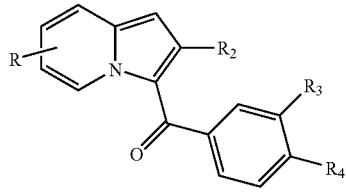

COMPOUNDS I
R₁ = H

BROMINATION

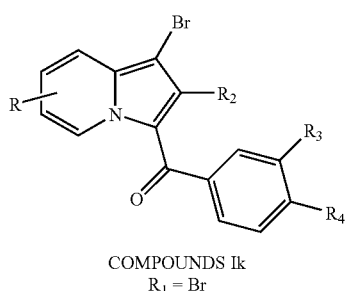

COMPOUNDS Ik
R₁ = Br

Ph—B(OH)₂
or heteroaryl-B(OH)₂
SUZUKI reaction

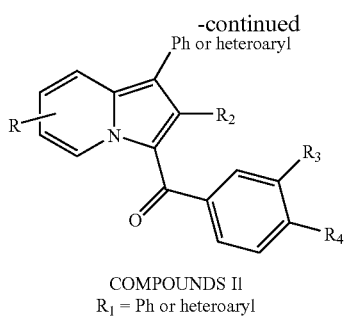

COMPOUNDS II
$R_1$ = Ph or heteroaryl

The compounds according to the invention, when $R_3$ or $R_4$ represents a nitro radical, are prepared with known benzoylation methods (*Eur. J. Med. Chem. Chim. Ther*, (1983), 18(4), pp 339-346) from an indolizine derivative of formula II, and a nitrobenzoyl chloride derivative, of formula III. The compounds of formula Ia are thus obtained.

The compounds of formula Id or Ig in which $R_3$ or $R_4$ represents an amino radical are obtained from the compounds of formula Ia by reducing the nitro functional group. By subjecting the compounds of formula Id to the action of an alkyl halide, the compounds of formula If are obtained for which $R_3$ or $R_4$ represents a radical —$NR_5R_6$ (in which $R_5$ represents a hydrogen atom and $R_6$ has the meanings given above).

By acylating the compounds of formula Id, the compounds of formula If are obtained for which $R_3$ or $R_4$ represents a radical —NH—CO-Alk.

By reacting an indolizine derivative of formula II with an alkoxycarbonylbenzoyl chloride derivative of formula III, the compounds of formula Ib are obtained in which $R_3$ or $R_4$ represents an alkoxycarbonyl radical. By subjecting the latter compounds to a saponification, the compounds of formula Ie are obtained in which $R_3$ or $R_4$ represents a carboxyl radical. If R optionally contains an ester functional group, the latter may also be saponified in order to obtain the corresponding acid.

By coupling the compounds of formula Ie with amines of formula $HNR_5R_6$ or hydroxylamine in the presence of a coupling agent, the compounds of formula Ip are obtained in which $R_3$ or $R_4$ represents a radical —CO—$NR_5R_6$ or —CO—NHOH.

By reacting an indolizine derivative of formula II with a trifluoroacetamidobenzoyl chloride derivative of formula III, the compounds of formula Ic are obtained in which $R_3$ or $R_4$ represents a trifluoroacetamide radical. By subjecting the latter compounds to a basic hydrolysis, the compounds of formula Id are obtained in which $R_3$ and/or $R_4$ represents a carboxyl and/or amino radical.

As represented in Scheme 2, starting with the compounds of formula Ia in which R represents a benzyloxy radical and $R_3$ or $R_4$ represent a nitro radical, by subjecting these compounds to a catalytic hydrogenation under pressure, the compounds of formula Ig are obtained where R represents a hydroxyl radical and $R_3$ or $R_4$ represents an amino radical.

By subjecting the compounds of formula Ig to a selective O-alkylation, the compounds of formula Ih are obtained in which R represents a linear alkoxy radical of 1 to 5 carbon atoms, or a radical —O-Alk-$COOR_7$. This latter radical can subsequently optionally be saponified in order to obtain a radical of formula —O-Alk-COOH.

As represented in Scheme 2, starting with the compounds of formula Ia in which R represents a hydroxyl radical and $R_3$ or $R_4$ represents a nitro radical, by subjecting these compounds to an O-alkylation, the compounds of formula Ii are obtained where R represents an alkoxy radical of 1 to 5 carbon atoms, a radical of formula —O-Alk-$COOR_7$ (which can then optionally be saponified in order to obtain a radical of formula —O-Alk-COOH), or a radical of formula —O-Alk-$NR_5R_6$ and $R_3$ or $R_4$ represents a nitro radical.

To obtain the compounds of formula Ij in which $R_1$ is a carboxyl radical, the compounds of formula I in which $R_1$ is an alkoxycarbonyl radical are subjected to a saponification.

As represented in Scheme 3, starting with the compounds of formula I in which $R_1$ represents a hydrogen atom and R, $R_3$ or $R_4$ have the meanings given in the general formula, the compounds of formula Ik where $R_1$ represents a bromine atom and R, $R_3$ or $R_4$ have the meanings given in the general formula are obtained by bromination. The latter compounds Ik when subjected (when R does not represent a bromine or iodine atom) to a Suzuki-type coupling with phenylboronic or heteroarylboronic derivatives lead to the derivatives of formula II where $R_1$ is a variously substituted phenyl radical or 5- or 6-membered heteroaryl and $R_3$ or $R_4$ have the meanings given in the general formula and R does not represent a bromine or iodine atom.

The compounds of formula II used, when $R_1$ represents a hydrogen atom, $R_2$ represents a methyl radical and R represents a radical —$CONH_2$ or $CO_2CH_3$, are described in *J. Chem. Soc. C*; (1969), 901.

The compounds of formula II, when $R_1$ represents a methoxy radical, $R_2$ represents a methyl radical and R represents a radical —$CONHCH_3$ at the 6-position or —$CON(CH_3)_2$ at the 6-position are prepared according to the following reaction schemes using the Tschitschibabin reaction (*Synthesis*, (1975), p 209) in order to prepare the indolizines:

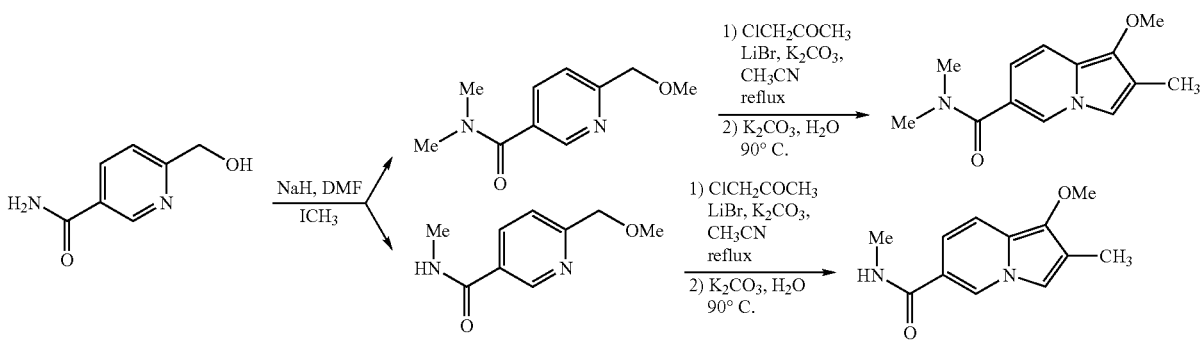

The compounds of formula II, when $R_1$ represents a hydrogen atom, $R_2$ represents a methyl radical and R represents either a radical —CONHCH$_3$ at the 6-position or a radical —NHCOOtBu at the 6-position, are prepared according to the following reaction scheme using the Tschitschibabin reaction (*Synthesis*, (1975), p 209) as above.

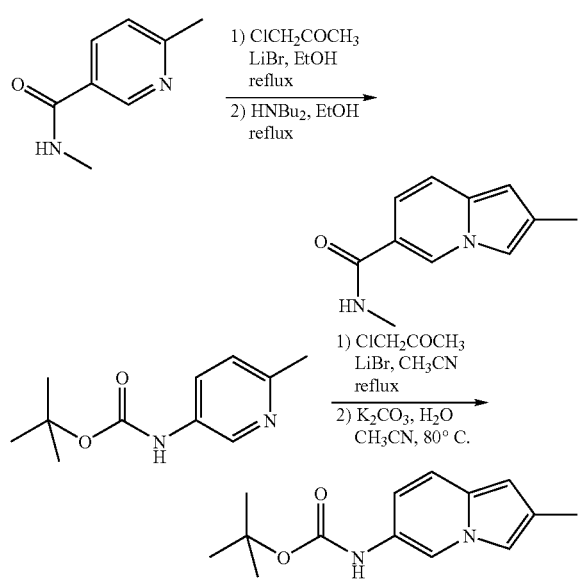

The compounds of formula II, when $R_1$ represents a radical —CO$_2$CH$_3$, $R_2$ represents a methyl radical and R either a benzyloxy radical at the 6-position or a benzyloxy radical at the 8-position, are also prepared using the Tschitschibabin reaction according to the following reaction schemes:

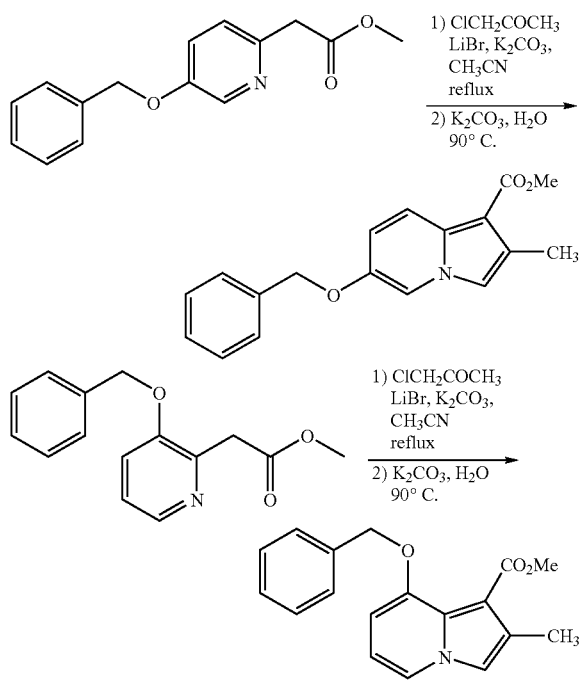

The compounds of formula Ia in which R represents a radical of formula —NH—COO-Alk at the 7-position and $R_1$ is an electron-attracting group such as benzyloxycarbonyl are prepared according to known cycloaddition methods [*J. Heterocyclic Chem.* (2001), 38, 853-857].

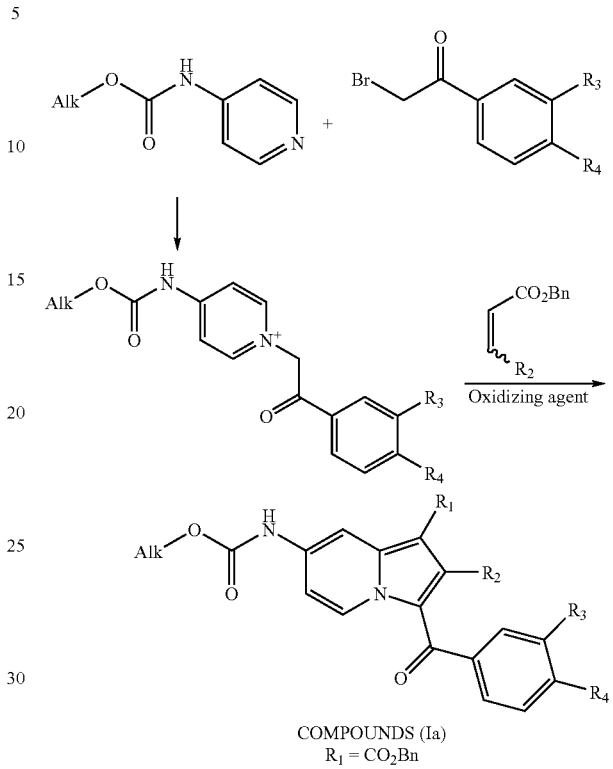

COMPOUNDS (Ia)
$R_1 = CO_2Bn$

The quaternization of the pyridines of formula IV with an appropriately substituted bromoacetophenone of formula V gives the pyridinium of formula VI. The 1,3-dipolar cycloaddition of the latter is carried out in the presence of an oxidizing agent such as manganese dioxide, in a polar solvent such as dimethylformamide.

The compounds of formula I are potent antagonists of FGF1 and 2. Their capacities to inhibit both the formation of new vessels from differentiated endothelial cells and to block the differentiation of CD34+ CD133+ adult human bone marrow cells into endothelial cells has been demonstrated in vitro. Furthermore, their capacity to inhibit pathological angiogenesis has been demonstrated in vivo. Moreover, it has been demonstrated that the compounds of formula I are potent antagonists of the FGF-1 receptor.

In general, the FGFs are greatly involved, via autocrine, paracrine or juxtacrine secretions, in the phenomena of deregulation of the stimulation of the growth of cancer cells. Furthermore, FGF receptors affect tumour angiogenesis which plays a preponderant role both in the growth of the tumour and also in the phenomena of metastasization Angiogenesis is a process of generation of new capillary vessels from preexisting vessels or by mobilization and differentiation of bone marrow cells. Thus, both an uncontrolled proliferation of endothelial cells and a mobilization of angioblasts from the bone marrow are observed in tumour neovascularization processes. It has been shown in vitro and in vivo that several growth factors stimulate endothelial proliferation, and in particular FGF1 or a-FGF and FGF2 or b-FGF. These two factors induce proliferation, migration and the production of proteases by endothelial cells in culture and neovascularization in vivo. a-FGF and b-FGF receptors interact with the endothelial cells via two classes of receptors, the high-affinity receptors with tyrosine kinase activity (FGFs) and the low-affinity receptors of the heparin sulfate proteoglycan (HSPG) type situated at the surface of the cells and in the extracellular matrices. While the paracrine role of these two factors on endothelial cells is widely described, a-FGF and b-FGF could also act on these cells through an autocrine process. Thus, a-FGF and b-FGF and their receptors represent very suitable targets for therapies aimed at inhibiting the angiogenesis process (Keshet E., Ben-Sasson S. A., *J. Clin. Invest.*, (1999), Vol. 501, pp. 104-1497; Presta M., Rusnati M., Dell'Era P., Tanghetti E., Urbinati C., Giuliani R. et al., *New York: Plenum Publishers*, (2000), pp. 7-34, Billottet C., Janji B., Thiery J. P., Jouanneau J., Oncogene, (2002), Vol. 21, pp. 8128-8139).

Moreover, systematic studies aimed at determining the expression due to a-FGF and b-FGF and of their receptors (FGF) on various types of tumour cells demonstrate that a cellular response to these two factors is functional in a great majority of human tumour lines studied. These results support the hypothesis that an antagonist of a-FGF and b-FGF could also inhibit the proliferation of tumour cells (Chandler L. A., Sosnowski B. A., Greenlees L., Aukerman S. L., Baird A., Pierce G. F., *Int. J. Cancer*, (1999), Vol. 58, pp. 81-451).

a-FGF and b-FGF play an important role in the growth and maintenance of prostate cells. It has been shown, both in animal models and in humans, that an alteration of the cellular response to these factors plays a crucial role in the progression of prostate cancer. Indeed, in these pathologies, both an increase in the production of a-FGF and b-FGF by the fibroblasts and the endothelial cells present in the tumour and an increase in the expression of the FGF receptors on tumour cells are recorded. Thus, a paracrine stimulation of prostate cancer cells occurs, and this process could be a major component of this pathology. A compound possessing an FGF receptor antagonizing activity such as the compounds of the present invention may represent a therapy of choice in these pathologies (Giri D., Ropiquet F., *Clin. Cancer Res.*, (1999), Vol. 71, pp. 5-1063; Doll J. A., Reiher F. K., Crawford S. E., Pins M. R., Campbell S. C., Bouck N. P., *Prostate*, (2001), Vol. 305, pp. 49-293).

Several studies show the presence of a-FGF and b-FGF and of their FGFR receptors both in human breast tumour lines (in particular MCF7) and in biopsies of tumours. These factors could be responsible, in this pathology, for the appearance of the very aggressive phenotype inducing high metastasization. Thus, a compound possessing an FGFR receptor antagonizing activity, such as the compounds of formula I, may represent a therapy of choice in these pathologies (Vercoutter-Edouart A-S., Czeszak X., Crepin M., Lemoine J., Boilly B., Le Bourhis X. et al., *Exp. Cell Res.*, (2001), Vol. 262, pp. 59-68).

Cancerous melanomas are tumours which induce metastases at a high frequency and which are very resistant to various chemotherapy treatments. The angiogenesis processes play a preponderant role in the progression of a cancerous melanoma. Furthermore, it has been shown that the probability of the appearance of metastases increases very strongly with the increase in the vascularization of the primary tumour. Melanoma cells produce and secrete various angiogenic factors, including a-FGF and b-FGF. Moreover, it has been shown that inhibition of the cellular effect of these two factors by the soluble FGFR1 receptor blocks in vitro the proliferation and the survival of melanoma tumour cells and blocks in vivo tumour progression. Thus, a compound possessing FGFR receptor antagonizing activity, such as the compounds of the present invention, may represent a therapy of choice in these pathologies (Rofstad E. K., Halsor E. F., *Cancer Res.*, (2000); Yayon A., Ma Y-S., Safran M., Klagsbrun M., Halaban R., *Oncogene*, (1997), Vol. 14, pp. 2999-3009).

Glioma cells produce in vitro and in vivo a-FGF and b-FGF and possess various FGF receptors at their surface. This therefore suggests that these two factors, through an autocrine and paracrine effect, play a pivotal role in the progression of this type of tumour. Furthermore, like the majority of solid tumours, the progression of gliomas and their capacity to induce metastases is highly dependent on the angiogenic processes in the primary tumour. It has also been shown that FGF-1 receptor antisenses block the proliferation of human astrocytomas. Furthermore, naphthalenesulfonate derivatives are described for inhibiting the cellular effects of a-FGF and b-FGF in vitro and the angiogenesis induced by these growth factors in vivo. Intracerebral injection of these compounds induces a very significant increase in apoptosis and a substantial decrease in angiogenesis resulting in considerable regression of gliomas in rats. Thus, a compound possessing an antagonist activity for a-FGF and/or b-FGF and/or the FGF receptors, such as the compounds of the present invention, may represent a therapy of choice in these pathologies (Yamada S. M., Yamaguchi F., Brown R., Berger M. S., Morrison R. S., *Glia*, (1999), Vol. 76, pp. 28-66; Auguste P., Gürsel D. B., Lemière S., Reimers D., Cuevas P., Carceller F., et al., *Cancer Res.*, (2001), Vol. 26, pp. 61-1717).

More recently, the potential role of proangiogenic agents in leukaemias and lymphomas has been documented. Indeed, it has been reported, in general, that cellular clones in these pathologies may be either naturally destroyed by the immune system or switch to an angiogenic phenotype which promotes their survival and then their proliferation. This change of phenotype is induced by an overexpression of angiogenic factors, in particular by the macrophages, and/or mobilization of these factors from the extracellular matrix (Thomas D. A., Giles F. J., Cortes J., Albitar M., Kantarjian H. M., *Acta Haematol*, (2001), Vol. 207, pp. 106-190). Among the angiogenic factors, b-FGF has been detected in numerous lymphoblastic and haematopoietic tumour cell lines. The FGF receptors are also present on a majority of these lines, suggesting a possible autocrine cellular effect of a-FGF and b-FGF inducing the proliferation of these cells. Moreover, it has been reported that bone marrow angiogenesis by paracrine effects was correlated with the progression of some of these pathologies.

More particularly, it has been shown, in CLL (chronic lymphocytic leukaemia) cells that b-FGF induces an increase in the expression of antiapoptotic protein (Bc12) leading to an increase in the survival of these cells and therefore greatly participates in their cancerization. Furthermore, the b-FGF levels measured in these cells are very well correlated with the stage of clinical progression of the disease and the resistance to the chemotherapy applied in this pathology (fludarabine). Thus, a compound possessing an FGF receptor antagonizing activity, such as the compounds of the present invention, may represent a therapy of choice, either in combination with fludarabine or other active products, in this pathology (Thomas D. A., Giles F. J., Cortes J., Albitar M., Kantarjian H. M., *Acta Haematol*, (2001), Vol. 207, pp. 106-190; Gabrilove J. L. *Oncologist*, (2001), Vol. 6, pp. 4-7).

A correlation exists between the process of bone marrow angiogenesis and the extramedullary diseases in CML (chronic myelomonocytic leukaemia). Various studies demonstrate that the inhibition of angiogenesis, in particular by a compound possessing an FGF receptor antagonizing activity could represent a therapy of choice in this pathology.

The proliferation and the migration of vascular smooth muscle cells contribute to intimal hypertrophy of the arteries and thus play a preponderant role in atherosclerosis and in restenosis following angioplasty and endarterectomy.

Studies in vivo show, after lesion of the carotid by balloon injury, a local production of a-FGF and b-FGF. In this same model, an anti-FGF2 neutralizing antibody inhibits the proliferation of vascular smooth muscle cells and thus decreases intimal hypertrophy.

A chimeric protein FGF2 bound to a molecule such as saporin inhibits the proliferation of vascular smooth muscle cells in vitro and intimal hypertrophy in vivo (Epstein C. E., Siegall C. B., Biro S., Fu Y. M., FitzGerald D., *Circulation*, (1991), Vol. 87, pp. 84-778; Waltenberger J., *Circulation*, (1997), pp. 96-4083).

Thus, antagonists of the FGF receptors, such as the compounds of the present invention, represent a therapy of choice, either alone or in combination with antagonist compounds for other growth factors involved in these pathologies, such as PDGF, in the treatment of pathologies linked to the proliferation of vascular smooth muscle cells such as atherosclerosis restenosis post-angioplasty or following the fitting of endovascular prostheses (stents) or during aorto-coronary artery by-pass surgery.

Cardiac hypertrophy occurs in response to a stress of the ventricular wall induced by an overload in terms of pressure or volume. This overload may be the consequence of numerous physiopathological states such as hypertension, AC (aortic coarctation), myocardial infarction and various vascular disorders. The consequences of this pathology are morphological, molecular and functional changes such as hypertrophy of cardiac myocytes, the accumulation of matrix proteins and the re-expression of foetal genes. b-FGF is involved in this pathology. Indeed, the addition of b-FGF to cultures of cardiomyocytes from newborn rats modifies the profile of the genes corresponding to contractile proteins leading to a foetal-type gene profile. Additionally, adult rat myocytes show a hypertrophic response under the effect of b-FGF, this response being blocked by anti-b-FGF neutralizing antibodies. Experiments carried out in vivo on transgenic knockout mice for b-FGF show that b-FGF is the major stimulating factor for cardiac myocyte hypertrophy in this pathology (Schultz JeJ., Witt S. A., Nieman M. L., Reiser P. J., Engle S. J., Zhou M. et al., *J. Clin. Invest.*, (1999), Vol. 19, pp. 104-709). Accordingly, a compound such as the compounds of the present invention, possessing FGF receptor antagonizing activity represents a therapy of choice in the treatment of cardiac insufficiency and any other pathology associated with a degeneracy of the cardiac tissue. This treatment could be carried out alone or in combination with current treatments (beta-blockers, diuretics, angiotensin antagonists, antiarrhythmics, anti-calcium agents, antithrombotics, and the like).

Vascular disorders caused by diabetes are characterized by an alteration of vascular reactivity and of blood flow, hyperpermeability, an exacerbated proliferative response and an increase in matrix protein deposits. More precisely, a-FGF and b-FGF are present in the preretinal membranes of patients with diabetic retinopathies, in the membranes of underlying capillaries and in the vitreous humour of patients suffering from proliferative retinopathies. A soluble FGF receptor capable of binding both a-FGF and b-FGF is developed in vascular disorders linked to diabetes (Tilton R. G., Dixon R. A. F., Brock T. A., *Exp. Opin. Invest. Drugs*, (1997), Vol. 84, pp. 6-1671). Thus, a compound such as the compounds of formula I possessing an FGF receptor antagonizing activity represents a therapy of choice either alone or in combination with antagonist compounds for other growth factors involved in these pathologies, such as VEGF.

Rheumatoid arthritis (RA) is a chronic disease with an unknown aetiology. While it affects numerous organs, the most severe form of RA is a progressive synovial inflammation of the joints leading to destruction. Angiogenesis appears to greatly affect the progression of this pathology. Thus, a-FGF and b-FGF have been detected in the synovial tissue and in the joint fluid of patients suffering from RA, indicating that this growth factor is involved in the initiation and/or progression of this pathology. In AIA models (adjuvant-induced model of arthritis) in rats, it has been shown that the overexpression of b-FGF increases the severity of the disease whereas an anti-b-FGF neutralizing antibody blocks the progression of RA (Yamashita A., Yonemitsu Y., Okano S., Nakagawa K., Nakashima Y., Irisa T. et al., *J. Immunol.*, (2002), Vol. 57, pp. 168-450; Manabe N., Oda H., Nakamura K., Kuga Y., Uchida S., Kawaguchi H., *Rheumatol*, (1999), Vol. 20, pp. 38-714). Thus, the compounds according to the invention represent a therapy of choice in this pathology.

IBDs (inflammatory bowel diseases) comprise two forms of chronic inflammatory diseases of the intestine: UC (ulcerative colitis) and Crohn's disease (CD). IBDs are characterized by an immune dysfunction which results in an inappropriate production of inflammatory cytokines inducing the establishment of a local microvascular system. The consequence of this angiogenesis of inflammatory origin is an intestinal ischaemia induced by vasoconstriction. High circulating and local levels of h-FGF have been measured in patients suffering from these pathologies (Kanazawa S., Tsunoda T., Onuma E., Majima T., Kagiyama M., Kkuchi K., *American Journal of Gastroenterology*, (2001), Vol. 28, pp. 96-822; Thorn M., Raab Y., Larsson A., Gerdin B., Hallgren R., *Scandinavian Journal of Gastroenterology*, (2000), Vol. 12, pp. 35-408). The compounds of the invention which exhibit a high antiangiogenic activity in a model of inflammatory angiogenesis represent a therapy of choice in these pathologies.

FGF-1, 2 and 3 receptors are involved in the processes of chronogenesis and osteogenesis. Mutations leading to the expression of permanently activated FGFRs have been linked to a large number of human genetic diseases which result in malformations of the skeleton, such as Pfeiffer, Crouzon, Apert, Jackson-Weiss and Bear-Stevenson cutis gyrata syndromes. Some of these mutations, which affect more particularly the FGF3 receptor, lead in particular to achondroplasia (ACH), hypochondroplasia (HCH) and TD (Thanatophoric dysplasia), ACH being the most common form of nanism. From a biochemical point of view, sustained activation of these receptors occurs through dimerization of the receptor in the absence of ligand (Chen. L., Adar R., Yang X., Monsonego E. O., LI C., Hauschka P. V., Yagon A. and Deng C. X., (1999), *The Journal of Clin. Invest.*, Vol. 104. No. 11, pp. 1517-1525). Thus, the compounds of the invention which exhibit an antagonist activity on the binding of b-FGF and FGFR and which thus inhibit the dimerization of the receptor represent a therapy of choice in these pathologies.

Moreover, it is known that the adipose tissue is one of the rare tissues which, in adults, can develop or regress. This tissue is highly vascularized and a very dense network of microvessels surrounds each adipocyte. These observations led to the testing of the effect of an antiangiogenic agent on the development of the adipose tissue in adults. Thus, it appears that in pharmacological models in ob/ob mice, the inhibition of angiogenesis results in a significant loss in the weight of the mice (Rupnick M. A. and al, (2002), *PNAS, Vol 99 no 16*, pp 10730-10735). Thus, an antagonist compound for the FGF receptors possessing a potent antiangiogenic activity may represent a therapy of choice in obesity-related pathologies.

By virtue of their low toxicity and their pharmacological and biological properties, the compounds of the present invention find application in the treatment of any carcinoma having a high degree of vascularization (lung, breast, prostate, oesophagus) or inducing metastases (colon, stomach, melanoma) or sensitive to a-FGF or to b-FGF in an autocrine manner or, finally, in lymphoma and leukaemia type pathologies. These compounds represent a therapy of choice either alone or in combination with an appropriate chemotherapy. The compounds according to the invention also find application in the treatment of cardiovascular diseases such as atherosclerosis, post-angioplasty restenosis, in the treatment of diseases linked to the complications which appear following the fitting of endovascular prostheses and/or aorto-coronary artery by-passes or other vascular transplants and cardiac hypertrophy or vascular complications of diabetes such as diabetic retinopathies. The compounds according to the invention also find application in the treatment of chronic inflammatory diseases such as rheumatoid arthritis or IBDs. Finally, the compounds according to the invention may be used in the treatment of achondroplasia (ACH), hypochondroplasia (HCH) and TD (thanatrophoric dysplasia), and also in the treatment of obesity.

The products according to the invention also find application in the treatment of macular degeneration. A major characteristic of loss of vision in adults is the neovascularization and the resulting haemorrhages which cause considerable functional disorders in the eye and which result in early blindness. Recently, the study of the mechanisms involved in the phenomena of ocular neovascularization has made it possible to demonstrate the involvement of a proangiogenic factor in these pathologies. By using a model of laser-induced choroidal neoangiogenesis, it was possible to confirm that the products according to the invention also make it possible to modulate the neovascularization of the choroid.

Moreover, the products of the invention may be used in the treatment or prevention of thrombocytopenia due in particular to an anticancer chemotherapy. It has indeed been demonstrated that the products of the invention can improve the level of circulating platelets during a chemotherapy.

According to another of its features, the subject of the present invention is a pharmaceutical composition containing, as active ingredient, a compound of formula I according to the invention or one of its pharmaceutically acceptable salts, optionally in combination with one or more inert and appropriate excipients.

The said excipients are chosen according to the pharmaceutical dosage form and the desired mode of administration: oral, sublingual, subcutaneous, intramuscular, intravenous, transdermal, transmucosal, local or rectal.

The pharmaceutical compositions according to the present invention are preferably administered by the oral route.

In the pharmaceutical compositions of the present invention for oral administration, the active ingredients may be administered in a unit form for administration, as a mixture with conventional pharmaceutical carriers. The appropriate unit forms for administration comprise, for example, tablets, which are optionally scored, gelatine capsules, powders, granules and oral solutions or suspensions.

When a solid composition in the form of tablets is prepared, the main active ingredient is mixed with a pharmaceutical vehicle such as gelatine, starch, lactose, magnesium stearate, talc, gum arabic and the like.

It is possible to coat the tablets with sucrose or other appropriate materials, or alternatively it is possible to treat them so that they have a prolonged or delayed activity and they continuously release a predetermined quantity of active ingredient.

A preparation in the form of gelatine capsules is obtained by mixing the active ingredient with a diluent and pouring the mixture obtained into soft or hard gelatine capsules.

A preparation in syrup or elixir form may contain the active ingredient together with a sweetener, preferably calorie-free, methylparaben and propylparaben as antiseptics, a taste enhancer and an appropriate colouring.

Water-dispersible powders or granules may contain the active ingredient as a mixture with dispersing agents, wetting agents or suspending agents, such as polyvinylpyrrolidone, and with sweeteners or flavour corrigents.

The active ingredient may also be formulated in the form of microcapsules, optionally with one or more carriers or additives.

In the pharmaceutical compositions according to the present invention, the active ingredient may also be in the form of an inclusion complex in cyclodextrins, their ethers or their esters.

The quantity of active ingredient to be administered depends, as always, on the degree of progression of the disease and the age and weight of the patient.

The compositions according to the invention, for oral administration, therefore contain recommended doses of 0.01 to 700 mg.

The following examples, given without limitation, illustrate the present invention.

PREPARATIONS

Preparations I and II

Synthesis of
6-(methoxymethyl)-N-methylnicotinamide and of
6-(methoxymethyl)-N,N-dimethynicotinamide A solution of 3.21 g (21.10 mmol) of 6-(hydroxymethyl) nicotinamide [described in *Bull. Chem. Soc. Jpn.*; (1988), 61(8), 2837-2846] in 90 ml of dimethylformamide is added dropwise at 0° C. to 1.56 g (42.19 mmol) of sodium hydride—at 65% as a dispersion in oil—in 23 ml of dimethylformamide, and the medium is stirred at 0° C. for 0.5 hour. Still at the same temperature, 2.63 ml (42.19 mmol) of methyl iodide in 7 ml of dimethylformamide are then added dropwise. Once the introduction is complete, the temperature is allowed to return to room temperature and the medium is stirred for 2 hours.

The reaction medium is poured over water and ethyl acetate.

The organic phase is separated by decantation, washed with a saturated aqueous sodium chloride solution, dried over sodium sulfate and concentrated under reduced pressure.

A mixture containing the two desired products is collected and separated by chromatography on a silica gel, eluting with a mixture of dichloromethane and methanol (95-5 and then 9-1).

The two fractions collected are then evaporated.

A) First Fraction: Preparation I 6-(methoxymethyl)-N,N-dimethylnicotinamide 1.27 g of a yellow oil are obtained.
Yield: 31%
Mass spectrometry (ES+mode) MH+=195.3

B) Second Fraction: Preparation II 6-(methoxymethyl)-N-methylnicotinamide 1.06 g of a yellow oil are obtained
Yield: 28%
Mass spectrometry (ES+mode) MH+=181.2

Preparation III

Synthesis of [1-methoxy-N,N,2-trimethylindolizin-6-yl]carboxamide

501 µL (6.29 mmol) of chloroacetone are added to a solution of 547 mg (6.29 mmol) of lithium bromide in 10 mL of acetonitrile and the medium is stirred for 15 minutes at room temperature and then 0.94 g (4.84 mmol) of 6-(methoxymethyl)-N,N-dimethylnicotinamide, obtained in Preparation I, dissolved in 10 mL of acetonitrile, is added and the medium is heated under reflux for 24 hours.

The reaction medium is evaporated to dryness. The residue is taken up in 20 mL of water and washed with ethyl ether.

After decantation, the aqueous phase is recovered, 1.34 g (9.71 mmol) of potassium carbonate are added and the medium is heated at 80° C. for 2 hours. Ethyl acetate is added, the medium is separated by decantation, the organic phase is washed with a saturated aqueous sodium chloride solution, dried over sodium sulfate and concentrated under reduced pressure.

The residue is purified by chromatography on a silica gel, eluting with a mixture of dichloromethane and methanol (95-5).

After evaporation, 960 mg of a yellow solid are recovered.
Yield: 67%
Melting point: 112.5° C.

Preparation IV

Synthesis of [1-methoxy-N,2-dimethylindolizin-6-yl]carboxamide

This compound is obtained according to the same procedure as the compound of Preparation III using the Tschitschibabin reaction, starting with 710 mg of 6-(methoxy-methyl)-N-methylnicotinamide obtained in Preparation II and chloroacetone. 1.03 g of a yellow solid are obtained.
Yield: 84%
Melting point: 127° C.

Preparation V

Synthesis of methyl [8-(benzyloxy)-2-methylindolizin-1-yl]carboxylate

This compound is obtained according to the same procedure as the compound of Preparation III using the Tschitschibabin reaction, starting with 25.82 g of methyl 2-[3-(benzyloxy)pyridin-2-yl]acetate [according to J. Med. Chem.; (1996), 39(19), 3636-3658] and chloroacetone.
19.11 g of a yellow solid are obtained.
Yield: 65%
Mass spectrometry (ES+mode) MH+=296

Preparation VI

Synthesis of methyl [6-(benzyloxy)-2-methylindolizin-1-yl]carboxylate

This compound is obtained according to the same procedure as the compound of Preparation III using the Tschitschibabin reaction, starting with 19 g of methyl 2-[5-(benzyloxy)pyridin-2-yl]acetate [according to Bull. Pol. Acad. Sci. Chem.; (1990), 38(1-12), 17-27] and chloroacetone. 15.01 g of an orange-coloured solid are obtained.
Yield: 69%
Melting point: 143° C.

Preparation VII

Synthesis of [N,2-dimethylindolizin-6-yl]carboxamide

This compound is obtained according to the same procedure as the compound of Preparation III using the Tschitschibabin reaction, starting with 5.4 g of 6-methyl-N-methylnicotinamide [described in J. Org. Chem.; (1959), 24, 1189-1191] and chloroacetone, using dibutylamine as base. 2.04 g of a yellow solid are obtained.
Yield: 32%
Mass spectrometry (ES+mode) MH+=189.4

Preparation VIII

Synthesis of tert-butyl [2-methylindolizin-6-yl]carbamate

This compound is obtained according to the same procedure as the compound of Preparation III using the Tschitschibabin reaction, starting with 5.79 g of tert-butyl (6-methylpyridin-3-yl)carbamate [described in J. Med. Chem.; (2000), 43, 5017-5029] and chloroacetone. 1.96 g of a pasty residue are obtained.
Yield: 31%
Mass spectrometry (ES+mode) MH+=247.1

Preparation IX

Synthesis of methyl [1-methoxy-2-methylindolizin-6-yl]carboxylate

Step A methyl 6-(methoxymethyl)nicotinate 5.1 g (0.022 mol) of methyl 6-(bromomethyl)nicotinate [described in J. Med. Chem.; (2002), 45(23), 5005-5022], dissolved in 60 mL of methanol are added at room temperature to a solution of sodium methoxide obtained by adding 1 g (0.044 atom/g) of sodium to 40 mL of methanol. The reaction medium is then heated under reflux for 2 hours. The reaction medium is concentrated under vacuum and the residue is taken up in an aqueous solution of potassium hydrogen sulfate and dichloromethane. The organic phase is separated by decantation, dried over sodium sulfate and evaporated to dryness. 3.4 g of a yellow solid are obtained.
Yield: 85%
Melting point: 33° C.
Step B 1.46 mL (0.0174 mol) of chloroacetone are added to 1.5 g (0.0174 mol) of lithium bromide in 10 mL of acetone and the medium is stirred at room temperature for 15 minutes and then 1.5 g (0.00828 mol) of methyl 6-(methoxymethyl)nicotinate are added and the medium is heated under reflux overnight. 1.5 g (0.0174 mol) of lithium bromide and 1.46 mL (0.0174 mol) of chloroacetone are added to the reaction medium and the medium is kept under reflux for 5 hours. The medium is evaporated to dryness and the residue obtained is taken up in a dichloromethane-methanol (9-1) mixture. The insoluble material obtained is filtered and then 4.62 mL (0.033 mol) of triethylamine are added to the filtrate and the medium is stirred at room temperature for one hour. The reaction medium is concentrated. The residue obtained is taken up in toluene and the product is purified by filtration on a silica bed, eluting with toluene. After evaporation, 450 mg of a yellow solid are obtained.

Yield: 25%

Melting point: 51° C.

EXAMPLES

Examples 1 and 2

Methyl [8-(benzyloxy)-3-(3-methoxy-4-nitrobenzoyl)-2-methylindolizin-1-yl]carboxylate (Example 1) and methyl [8-hydroxy-3-(3-methoxy-4-nitrobenzoyl)-2-methylindolizin-1-yl]carboxylate (Example 2)

18.1 g (0.0841 mol) of 3-methoxy-4-nitrobenzoyl chloride are added to 19.1 g (0.0647 mol) of methyl [8-(benzyloxy)-2-methylindolizin-1-yl]carboxylate dissolved in 100 mL of 1,2-dichloromethane and the medium is stirred at room temperature for 60 hours.

The reaction medium is evaporated to dryness. A mixture of two products is recovered and separated by chromatography on a silica gel, eluting with a toluene-ethyl acetate (9-1) mixture. This separation is followed by thin-layer chromatography (TLC) using, as eluent, a mixture of dichloromethane and methanol (9-1).

Each of the two fractions is then evaporated:

A) First Fraction

Methyl [8-(benzyloxy)-3-(3-methoxy-4-nitrobenzoyl)-2-methylindolizin-1-yl]carboxylate 8.71 g of an orange-coloured solid are obtained.
Yield: 28%
Melting point: 125° C.

B) Second Fraction

Methyl [8-hydroxy-3-(3-methoxy-4-nitrobenzoyl)-2-methylindolizin-1-yl]carboxylate 7.68 g of an orange-coloured solid are obtained.
Yield: 31%
Melting point: 150° C.

Examples 3 to 17

By carrying out the procedure according to the preparation described above, the compounds of formula I, which are described in Table I below, are synthesized by benzoylation of the 3-position of the indolizines, variously substituted at the 1-, 2-, 6-, 7- and 8-position with suitably substituted benzoyl chlorides.

TABLE I

| Example | R | $R_1$ | $R_2$ | $R_3$ | $R_4$ | Yield (%) | Melting point (° C.) or Mass spectro (ES+ mode) |
|---|---|---|---|---|---|---|---|
| 3 | 6-O—Bn | $CO_2Me$ | Me | OMe | $NO_2$ | 93 | 179° C. |
| 4 | 7-Me | $CO_2Me$ | Me | OMe | $NO_2$ | 85 | 152° C. |
| 5 | 6-CONHMe | OMe | Me | OMe | $NO_2$ | 97.5 | MH+ = 398.2 |
| 6 | 6-CONHMe | OMe | Me | $CO_2Me$ | $NHCOCF_3$ | 56 | 241° C. |
| 7 | 6-CONMe$_2$ | OMe | Me | OMe | $NO_2$ | 95 | 128° C. |
| 8 | 6-CONMe$_2$ | OMe | Me | $CO_2Me$ | $NHCOCF_3$ | 78.5 | MH+ = 506.2 |
| 9 | 6-OMe | OMe | Me | $CO_2Me$ | $NHCOCF_3$ | 60 | MH+ = 465.1 |
| 10 | 6-$CO_2Me$ | OMe | Me | OMe | $NO_2$ | 85 | 211° C. |
| 11 | 6-CONHMe | H | Me | OMe | $NO_2$ | 77 | 236° C. |
| 12 | 6-$CONH_2$ | H | Me | OMe | $NO_2$ | 76 | 286° C. |
| 13 | 6-$CONH_2$ | H | Me | $CO_2Me$ | $NO_2$ | 99 | 240° C. |
| 14 | 6-$CO_2Me$ | H | Me | $CO_2Me$ | $NHCOCF_3$ | 72 | 215° C. |
| 15* | 6-NH—BOC | H | Me | OMe | $NO_2$ | 59 | 104° C. |
| 16 | H | H | Me | $CO_2Me$ | $NO_2$ | 88 | 168° C. |
| 17 | H | H | Me | $CO_2Me$ | $NHCOCF_3$ | 37 | 167° C. |

*benzoylation in the presence of triethylamine (1 equivalent)
Bn = benzyl
Me = methyl
BOC = tert-butyloxycarbonyl

Example 18

[1-methoxy-3-(3-methoxy-4-nitrobenzoyl)-2-methylindolizin-6-yl]carboxamide

Step A

[1-Methoxy-3-(3-methoxy-4-nitrobenzoyl)-2-methylindolizin-6-yl]carboxylic Acid 1.21 mL (0.00121 mol) of 1N sodium hydroxide are added to 440 mg (0.0011 mol) of methyl [1-methoxy-3-(3-methoxy-4-nitrobenzoyl)-2-methylindolizin-6-yl]carboxylate (obtained in Example 10) in 10 mL of methanol and the medium is stirred at room temperature overnight. The reaction medium is concentrated under vacuum and the residue is taken up in water and ethyl acetate. The aqueous phase is separated by decantation and then acidified with 1.21 mL of 1N hydrochloric acid. The precipitate formed is filtered, washed with water and dried. 280 mg of an orange-coloured solid are obtained.

Yield: 66%

Melting point: 287° C.

Step B

104 μl (0.74 mmol) of triethylamine and then 330 mg (0.74 mmol) of benzotriazol-1-yloxy-tris(dimethylamino)phosphonium hexafluorophosphate (BOP) are added to 260 mg (0.66 mmol) of [1-methoxy-3-(3-methoxy-4-nitrobenzoyl)-2-methylindolizin-6-yl]carboxylic acid in 5 mL of N,N-dimethylformamide and the medium is stirred for one hour at room temperature. 0.9 mL (2.71 mmol) of a 3N solution of ammonia in tetrahydrofuran is added to the reaction medium and the medium is kept stirred at room temperature overnight. Water and a saturated aqueous sodium bicarbonate solution are added. The medium is extracted several times with ethyl acetate. The organic phase is separated by decantation, dried over sodium sulfate and concentrated under vacuum. The solid residue obtained is taken up in isopropyl ether, filtered, washed with isopropyl ether and then dried. 210 mg of a red solid are obtained.

Yield: 81%

Melting point: 244° C.

Example 19

Methyl [8-methoxy-3-(3-methoxy-4-nitrobenzoyl)-2-methylindolizin-1-yl]carboxylate 0.19 mL (2.02 mmol) of dimethyl sulfate is added to a mixture of 705 mg (1.84 mmol) of methyl [8-hydroxy-3-(3-methoxy-4-nitrobenzoyl)-2-methylindolizin-1-yl]carboxylate obtained in Example 2, in 10 mL of acetone with 330 mg (2.39 mmol) of potassium carbonate and the medium is heated at 60° C. for 6 hours.

The medium is evaporated. The oil obtained is taken up in ethyl acetate and in water.

The organic phase is separated by decantation, washed with water and then with a saturated aqueous sodium chloride solution, dried over sodium sulfate and concentrated under reduced pressure. The solid obtained is taken up in isopropyl ether, filtered, washed with isopropyl ether and then dried. 649 mg of a yellow solid are recovered.

Yield: 88%

Melting point: 73° C.

Examples 20 and 21

By carrying out the procedure according to the preparation described above, the compounds of formula Ii, which are described in Table II below, are synthesized by O-alkylation of the hydroxyl at the 8-position of the indolizines variously substituted with suitable alkyl halides.

TABLE II

| Example | R | $R_1$ | $R_2$ | $R_3$ | $R_4$ | Yield (%) | Melting point (° C.) |
|---|---|---|---|---|---|---|---|
| 20 | 8-OCH$_2$CO$_2$Et | CO$_2$Me | Me | OMe | NO$_2$ | 98 | 191 |
| 21 | 8-O(CH$_2$)$_2$NMe$_2$ | CO$_2$Me | Me | OMe | NO$_2$ | 55 | 186 |

Example 22

(3-methoxy-4-nitrophenyl)[1-(4-methoxyphenyl)-2-methylindolizin-3-yl]methanone

Step A (3-methoxy-4-nitrophenyl)(2-methylindolizin-3-yl)methanone

This compound is obtained by carrying out the procedure according to the preparation described in Example 1, by benzoylation of 2-methylindolizine, described in *Pharmazie*; (1980), *vol* 35(4), pp 203-204, with 3-methoxy-4-nitrobenzoyl chloride.

6.52 g of an orange-coloured solid are obtained.

Yield: 92%

Melting point: 161° C.

Step B (3-methoxy-4-nitrophenyl)(1-bromo-2-methylindolizin-3-yl)methanone

A solution of 993 μL (19.39 mmol) of bromine in 35 mL of dioxane is added dropwise to 5.47 g (17.63 mmol) of (3-methoxy-4-nitrophenyl)(2-methylindolizin-3-yl)methanone, obtained in step A above, in 56 mL of dioxane while keeping the reaction medium at room temperature. Once the introduction is complete, the medium is stirred for a further 1 hour at the same temperature.

The reaction medium is poured over a saturated aqueous sodium bicarbonate solution and extracted with ethyl acetate. The organic phase is separated by decantation, washed with a saturated aqueous sodium chloride solution, dried over sodium sulfate and concentrated under reduced pressure.

The residue is taken up in dichloromethane and the product is purified by filtration on a bed of silica gel.

After evaporation, 6.75 g of a yellow solid are recovered.

Yield: 98%

Melting point: 166° C.

Step C (3-methoxy-4-nitrophenyl)[1-(4-methoxyphenyl)-2-methylindolizin-3-yl]methanone 59.4 mg (0.05 mmol) of tetrakis(triphenylphosphine)palladium(0) are added to 500 mg (1.28 mmol) of (3-methoxy-4-nitrophenyl)(1-bromo-2-methylindolizin-3-yl)methanone, obtained in the preceding step B, in 4.3 mL of dimethoxyethane, under an argon atmosphere, in the presence of 3 mL of a 1 N aqueous sodium carbonate solution, followed by 238 mg (1.57 mmol) of 4-methoxyphenylboronic acid and the medium is heated under reflux for 2 hours.

The reaction medium is poured over water and extracted with ethyl acetate. The organic phase is separated by decantation, washed with a saturated aqueous sodium chloride solution, dried over sodium sulfate and concentrated under reduced pressure.

The product is purified by chromatography on silica gel, eluting with a mixture of toluene and ethyl acetate (92-8).

After evaporation, 500 mg of an orange-coloured solid are recovered.

Yield: 93.5%

Melting point: 169° C.

Examples 23 to 29

By carrying out the procedure according to the preparation described above (Example 22 Step B), the compounds of formulae Ik, which are described in Table III below, are synthesized by bromination of the compounds of formula I (with $R_1$=H) with bromine.

TABLE III

| Example | R | $R_1$ | $R_2$ | $R_3$ | $R_4$ | Yield (%) | Melting point (° C.) |
|---|---|---|---|---|---|---|---|
| 23 | 6-CONHMe | Br | Me | OMe | $NO_2$ | 100 | dec. 205 |
| 24 | 6-$CONH_2$ | Br | Me | OMe | $NO_2$ | 100 | 277 |
| 25 | 6-$CONH_2$ | Br | Me | $CO_2Me$ | $NO_2$ | 85 | 242 |
| 26 | 6-$CO_2Me$ | Br | Me | $CO_2Me$ | $NHCOCF_3$ | 88 | 241 |
| 27** | 6-NH—BOC | Br | Me | OMe | $NO_2$ | 98 | 117 |
| 28 | H | Br | Me | $CO_2Me$ | $NO_2$ | 88 | 187 |
| 29 | H | Br | Me | $CO_2Me$ | $NHCOCF_3$ | 98 | 168 |

**the bromination is carried out in the presence of sodium acetate

Examples 30 to 46

By carrying out the procedure according to the preparation described in Example 22 Step C, the compounds of formulae II, which are described in Table IV below, are synthesized by Suzuki-type coupling of the brominated compounds of general formula Ik with phenylboronic or heteroarylboronic derivatives while varying the experimental conditions (catalysts, ligands, bases) according to the compounds to be obtained.

TABLE IV

| EX | R | $R_1$ | $R_2$ | $R_3$ | $R_4$ | Catalyst/ligand/base | Yield (%) | mp (° C.) |
|---|---|---|---|---|---|---|---|---|
| 30 | H | Ph-3-OMe | Me | OMe | $NO_2$ | $Pd(PPh_3)_4/Na_2CO_3$ | 95 | 65 |
| 31 | H | Ph-3-OMe | Me | $CO_2Me$ | $NO_2$ | $Pd(PPh_3)_4/Na_2CO_3$ | 65 | 187 |
| 32 | H | Ph-2,3,4-triOMe | Me | $CO_2Me$ | $NO_2$ | $Pd(PPh_3)_4/Na_2CO_3$ | 23 | 157 |
| 33 | H | Ph-3,4,5-triOMe | Me | $CO_2Me$ | $NO_2$ | $Pd(PPh_3)_4/Na_2CO_3$ | 51 | 195 |
| 34 | 6-CONH2 | Ph-4-OMe | Me | $CO_2Me$ | $NO_2$ | $Pd(PPh_3)_4/Na_2CO_3$ | 51 | 243 |
| 35 | 6-CONH2 | Ph-4-OMe | Me | OMe | $NO_2$ | $Pd(PPh_3)_4/Na_2CO_3$ | 76 | 267 |
| 36 | 6-CONHMe | Ph-4-OMe | Me | OMe | $NO_2$ | $Pd(PPh_3)_4/Na_2CO_3$ | 93 | 227 |
| 37 | 6-NH—BOC | Ph-4-OMe | Me | OMe | $NO_2$ | $Pd(PPh_3)_4/Na_2CO_3$ | 91 | 104 |
| 38 | H | 3-thienyl | Me | OMe | $NO_2$ | $Pd(PPh_3)_4/Na_2CO_3$ | 89 | 192 |
| 39 | H | 3-furyl | Me | OMe | $NO_2$ | $Pd(PPh_3)_4/Na_2CO_3$ | 68 | 152 |
| 40 | H | 2-thienyl | Me | OMe | $NO_2$ | $Pd_2dba_3, Pd(tBu_3)_2$ $Na_2CO_3$ | 65 | 154 |
| 41* | H | 4-pyridyl | Me | OMe | $NO_2$ | $PdCl_2(dppf).CH_2Cl_2$ $Na_2CO_3$ | 55 | 213 |
| 42* | H | 3-pyridyl | Me | OMe | $NO_2$ | $PdCl_2(dppf).CH_2Cl_2$ $Na_2CO_3$ | 65 | 213 |
| 43** | H | Ph-4-OMe | Me | $CO_2Me$ | $NH_2$ | $Pd(PPh_3)_4/Na_2CO_3$ | 89 | 187 |
| 44** | 6-$CO_2Me$ | Ph-4-OMe | Me | $CO_2Me$ | $NH_2$ | $Pd(PPh_3)_4/Na_2CO_3$ | 57 | 198 |
| 45** | H | 3-thienyl | Me | $CO_2Me$ | $NH_2$ | $Pd(PPh_3)_4/Na_2CO_3$ | 43 | 189 |
| 46** | H | 2-thienyl | Me | $CO_2Me$ | $NH_2$ | $Pd_2dba_3, Pd(tBu_3)_2$ $K_3PO_4$ | 81 | 162 |

Ph = phenyl
Bu = butyl
*the derivatives, pinacol boronates, are used instead of the corresponding boronic acids
**loss of the trifluoroacetyl protecting group during the synthesis in a basic medium

Example 47

Benzyl [7-{N-(tert-butoxycarbonyl)amino}-3-(3-methoxy-4-nitrobenzoyl)-2-methylindolizin-1-yl] carboxylate Step A 4-[N-(tert-butoxycarbonyl)amino]-1-[2-(3-methoxy-4-nitrophenyl)-2-oxoethyl]pyridinium Bromide 2.90 g (10.6 mmol) of 2-bromo-1-(3-methoxy-4-nitrophenyl)-1-ethanone [described in *Bull. Soc. Chim. Fr.*, (1962), pp 2255-2261] are added in portions to 2.07 g (10.6 mmol) of 4-[N-(tert-butoxycarbonyl)amino]pyridine [described in *Tetrahedron*; (2001), *vol* 57(43), pp 9033-9044] in suspension in 10 mL of acetonitrile and 20 mL of acetone. The reaction medium becomes homogeneous by stirring at room temperature and then precipitation occurs. The medium is stirred for 1 hour at room temperature. The precipitate formed is filtered, washed with acetone and dried. 4.6 g of a white powder are obtained.

Yield: 93%
Melting point: 224° C.

Step B 9.4 g (53.38 mmol) of benzyl crotonate, 1.8 mL (12.8 mmol) of triethylamine and 3.7 g (42.68 mmol) of manganese oxide are successively added to a solution of 5.0 g (10.67 mmol) of 4-[N-(tert-butoxycarbonyl)amino]-1-[2-(3-methoxy-4-nitrophenyl)-2-oxoethyl]pyridinium bromide in 40 mL of dimethylformamide. The reaction mixture is then heated at 90° C. for 4 hours and then filtered on a silica bed, eluting with ethyl acetate. The filtrate is poured over water and extracted with ethyl acetate. After decantation, the organic phase is washed with a saturated sodium chloride solution, dried over sodium sulfate and then concentrated under reduced pressure. The product is purified by chromatography on silica gel, eluting with a toluene/ethyl acetate (95/5 to 70/30) mixture. 2.6 g of an orange-coloured powder are obtained.

Yield: 44%

Melting point: 95° C.

Example 48

Benzyl [7-{N-(ethoxycarbonyl)amino}-3-(3-methoxy-4-nitrobenzoyl)-2-methylindolizin-1-yl]carboxylate Step A 4-[N-(ethoxycarbonyl)amino]-1-[2-(3-methoxy-4-nitrophenyl)-2-oxoethyl]pyridinium Bromide This compound is prepared according to the same method as that described in Example 47, Step A by quaternization of 1.21 g (7.33 mmol) of ethyl 4-pyridinylcarbamate [described in *J. Chem. Soc.*; (1962), 2379-2381] with 2-bromo-1-(3-methoxy-4-nitrophenyl)-1-ethanone in dichloromethane. 3.24 g of a white precipitate are obtained.

Yield: 100%

Mass spectrometry (ES+mode) MH$^+$=360.3

Step B

This compound is prepared according to the same method as that described in Example 47 Step B from 1.8 g (4.1 mmol) of 4-[N-(ethoxycarbonyl)amino]-1-[2-(3-methoxy-4-nitrophenyl)-2-oxoethyl]pyridinium bromide with benzyl crotonate in the presence of manganese oxide as oxidizing agent. 573 mg of a yellow powder are obtained.

Yield: 26%

Melting point: 182° C.

Example 49

Benzyl [7-amino-3-(3-methoxy-4-nitrobenzoyl)-2-methylindolizin-1-yl]carboxylate 26 mL of trifluoroacetic acid are added to 8.34 g (14.9 mmol) of benzyl [7-N-[(tert-butoxycarbonyl)amino]-3-(3-methoxy-4-nitrobenzoyl)-2-methylindolizin-1-yl]-carboxylate in solution in 40 mL of dichloromethane. The solution is stirred for 2 hours at room temperature, and the reaction medium is poured over a saturated aqueous sodium bicarbonate solution. The brick-red solid obtained is filtered and it is abundantly washed with water and then dried. The product is adsorbed onto silica and purified by chromatography on a silica gel, eluting with dichloromethane-methanol (97-3). 6.3 g of a red solid are obtained.

Yield: 92%

Melting point: 260-274° C. (decomposition)

Example 50

(4-amino-3-methoxyphenyl)[6-amino-1-(4-methoxyphenyl)-2-methylindolizin-3-yl]methanone This compound is prepared according to the same method as that described in Example 49 by unblocking tert-butyl [3-(4-amino-3-methoxybenzoyl)-1-(4-methoxyphenyl)-2-methylindolizin-6-yl]carbamate with trifluoroacetic acid.

317 mg of a yellow solid are obtained.

Yield: quantitative

Melting point: 182° C.

Example 51

Benzyl [7-(acetylamino)-3-(3-methoxy-4-nitrobenzoyl)-2-methylindolizin-1-yl]carboxylate A suspension of 1.5 g (3.26 mmol) of benzyl [7-amino-3-(3-methoxy-4-nitrobenzoyl)-2-methylindolizin-1-yl]carboxylate in 10 mL of acetic anhydride is heated at 100° C. for 15 minutes.

The mixture becomes homogeneous. The reaction mixture is cooled and then the precipitate formed is filtered.

The solid obtained is washed with dichloromethane and isopropyl ether and then adsorbed onto silica and purified by chromatography on silica gel, eluting with a mixture of toluene and ethyl acetate (100/0 to 50/50).

994 mg of an orange-coloured solid are obtained.

Yield: 61%

Melting point: 227° C.

Example 52

Benzyl [3-(3-methoxy-4-nitrobenzoyl)-2-methyl-7-[(methylsulfonyl)amino)]indolizin-1-yl]carboxylate 410 μL (5.32 mmol) of mesyl chloride are added to 1.22 g (2.66 mmol) of benzyl [7-amino-3-(3-methoxy-4-nitrobenzoyl)-2-methylindolizin-1-yl]carboxylate in 15 mL of pyridine. The reaction mixture is heated at 70° C. for 2.5 hours, and then cooled to room temperature and concentrated under reduced pressure.

The residue obtained is dissolved in dichloromethane and washed with a molar solution of hydrochloric acid.

After decantation, the organic phase is washed with a saturated aqueous sodium chloride solution, dried over sodium sulfate and concentrated under reduced pressure.

The product is adsorbed onto silica and purified by chromatography on a silica gel, eluting with a mixture of dichloromethane and methanol (9/1). 348 mg of a brown powder are obtained.

Yield: 24%

Melting point: 221° C.

Example 53

Benzyl [7-[(N-tert-butoxycarbonyl)(N-methyl)amino]-3-(3-methoxy-4-nitrobenzoyl)-2-methylindolizin-1-yl]carboxylate 154 mg (3.54 mmol) of sodium hydride (60% as a dispersion in oil) at room temperature are added in portions to 1.33 g (2.34 mmol) of benzyl [7-[(N-tert-butoxycarbonyl)amino]-3-(3-methoxy-4-nitrobenzoyl)-2-methylindolizin-1-yl]carboxylate in 10 mL of tetrahydrofuran.

After 15 minutes, 220 μL (3.54 mmol) of methyl iodide are added to the solution. The reaction mixture is stirred at 40° C. for 2 hours and then cooled and poured into a molar solution of hydrochloric acid and then extracted with ethyl acetate.

The organic phase is washed with a saturated aqueous sodium chloride solution, dried over sodium sulfate and concentrated under reduced pressure. The product is adsorbed onto silica and purified by chromatography on a silica gel, eluting with dichloromethane/methanol (9/1). 505 mg of an orange-coloured solid are obtained.

Yield: 64%
Melting point: 117° C.

Example 54

Benzyl [3-(3-methoxy-4-nitrobenzoyl)-2-methyl-7-(methylamino)indolizin-1-yl]-carboxylate This compound is obtained according to the same method as the compound of Example 49 by deprotection of the amino functional group of 849 mg (1.48 mmol) of benzyl [7-[(N-tert-butoxycarbonyl)(N-methyl)amino]-3-(3-methoxy-4-nitrobenzoyl)-2-methylindolizin-1-yl]carboxylate with trifluoroacetic acid. 549 mg of an orange-coloured powder are obtained.

Yield: 78%
Melting point: 228° C.

Example 55

Benzyl [7-(dimethylamino)-3-(3-methoxy-4-nitrobenzoyl)-2-methylindolizin-1-yl]-carboxylate 80 mg (1.67 mmol) of sodium hydride (60% as a dispersion in oil) at room temperature are added in portions to 525 mg (1.11 mmol) of benzyl [3-(3-methoxy-4-nitrobenzoyl)-2-methyl-7-methylaminoindolizin-1-yl]carboxylate in solution in 10 mL of dimethylformamide. After 10 minutes, 138 μL (2.22 mmol) of methyl iodide are added to the reaction mixture. The medium is stirred at 40° C. for 2 hours, poured into a molar solution of hydrochloric acid and then extracted with ethyl acetate. The organic phase is washed with a saturated aqueous sodium chloride solution, dried over sodium sulfate and concentrated under reduced pressure. The solid obtained is taken up in dichloromethane and filtered. 439 mg of a light orange-coloured solid are obtained.

Yield: 81%
Melting point: 167° C.

Example 56

(4-amino-3-methoxyphenyl)[1-(4-methoxyphenyl)-2-methylindolizin-3-yl]methanone 92 mg of 10% Pd/C are added to 460 mg (1.1 mmol) of (3-methoxy-4-nitrophenyl)[1-(4-methoxyphenyl)-2-methylindolizin-3-yl]methanone, compound of Example 22, in 9 mL of ethanol, followed by 1.12 mL (10.05 mmol) of cyclohexane and the medium is heated under reflux for 4 hours. The reaction medium is cooled, filtered on talc and the catalyst is washed with dichloromethane. The filtrate is concentrated under reduced pressure. The product is purified by chromatography on a silica gel, eluting with a mixture of toluene and ethyl acetate (9-1 and then 8-2).

400 mg of a yellow powder are obtained.

The powder is salified by dissolving the powder previously obtained in dioxane and then adding 1.18 mL (1.2 equivalents) of 1 N hydrochloric acid in ethyl ether. After addition of ethyl ether, the precipitate obtained is filtered, washed with ethyl ether and then dried. 400 mg of a yellow powder are recovered in hydrochloride form.

Yield: 94%
Melting point: 222.5° C.

Examples 57 to 66

By carrying out the procedure according to the preparation described above, the compounds described in Table V below are synthesized by reducing the nitro functional group of the compounds of formula Ia with cyclohexane in the presence of 10% Pd/C as catalyst.

TABLE V

| Example | R | $R_1$ | $R_2$ | $R_3$ | $R_4$ | Yield (%) | Salts | Melting point ° C. |
|---|---|---|---|---|---|---|---|---|
| 57 | H | Ph-3-OMe | Me | OMe | $NH_2$ | 94 | HCl, 0.35 $H_2O$ | 219 |
| 58 | 6-CONHMe | OMe | Me | OMe | $NH_2$ | 97 | HCl, 0.6 $H_2O$ | 231 |
| 59 | 6-CONMe$_2$ | OMe | Me | OMe | $NH_2$ | 70 | HCl | 222.5 |
| 60 | 7-Me | $CO_2Me$ | Me | OMe | $NH_2$ | 97 | — | 162 |
| 61 | 8-OMe | $CO_2Me$ | Me | OMe | $NH_2$ | 85 | HCl | 190 |
| 62 | 8-OCH$_2$CO$_2$Et | $CO_2Me$ | Me | OMe | $NH_2$ | 81 | — | 136 |
| 63 | 6-CONH$_2$ | OMe | Me | OMe | $NH_2$ | 86 | 0.8HCl | 198 |
| 64 | 6-CO$_2$Me | OMe | Me | OMe | $NH_2$ | 90 | — | 193 |
| 65 | 6-CONH$_2$ | Ph-4-OMe | Me | $CO_2Me$ | $NH_2$ | 65 | — | 275 |
| 66 | H | Ph-3-OMe | Me | $CO_2H$ | $NH_2$ | 42 | Na, 1.5 $H_2O$ | 253 |

Example 67

Methyl [3-(4-amino-3-methoxybenzoyl)-6-(benzyloxy)-2-methylindolizin-1-yl]carboxylate 0.4 mL of acetic acid and 200 mg of iron are added to 441 mg (0.93 mmol) of methyl [6-(benzyloxy)-3-(3-methoxy-4-nitrobenzoyl)-2-methylindolizin-1-yl]carboxylate in solution in a mixture of 4 mL of water and 8 mL of ethanol.

The medium is heated at 70° C. for 3 hours and then allowed to return to room temperature before pouring the reaction medium over water and extracting with dichloromethane.

The organic phase is washed with a saturated sodium chloride solution, dried over sodium sulfate and then concentrated under reduced pressure. The 410 mg of yellow solid are salified in hydrochloride form.

A yellow solid (hydrochloride) is obtained.
Yield: 80%
Melting point: 204° C.

Examples 68 and 69

By carrying out the procedure according to the preparation described above, the compounds described in Table VI below are synthesized by reducing the nitro functional group of the compounds of formula Ia with iron and acetic acid in ethanol.

TABLE VI

| Example | R | $R_1$ | $R_2$ | $R_3$ | $R_4$ | Yield (%) | Salts | Melting point ° C. |
|---|---|---|---|---|---|---|---|---|
| 68 | H | 4-pyridyl | Me | OMe | $NH_2$ | 99 | 2HCl, 2.6 $H_2O$ | 216 |
| 69 | H | 3-pyridyl | Me | OMe | $NH_2$ | 89 | 2HCl, 2.25 $H_2O$ | 212 |

Example 70

[3-(4-amino-3-methoxybenzoyl)-1-(4-methoxyphenyl)-2-methylindolizin-6-yl]-carboxamide 184 mg of 10% Pd/C in suspension in 4 mL of methanol are first of all added to 880 mg (1.92 mmol) of [3-(3-methoxy-4-nitrobenzoyl)-1-(4-methoxyphenyl)-2-methylindolizin-6-yl]carboxamide in 15 mL of methanol and 13 mL of dichloromethane, followed by 470 µl (9.60 mmol) of hydrazine hydrate and the medium is stirred at room temperature overnight. The reaction medium is filtered on talc and the catalyst is washed with methanol.

The filtrate is concentrated under reduced pressure. The residue is purified by flash chromatography on a silica column, eluting with a dichloromethane-methanol (98-2) and then (95-5) mixture. The pure fractions are concentrated under reduced pressure and 610 mg of a yellow powder are recovered.

The product is salified by adding 1N hydrochloric acid in ethyl ether. After addition of ethyl ether, the precipitate obtained is filtered, washed with ethyl ether and then dried. A yellow solid is recovered in the form of a hydrochloride hydrate (1.35$H_2O$).
Yield: 74%
Melting point: 213° C.

Examples 71 to 77

By carrying out the procedure according to the preparation described in Example 70, the compounds described in Table VII below are synthesized by reducing the nitro functional group of the compounds of formula Ia with hydrazine hydrate in the presence of 10% Pd/C as catalyst.

TABLE VII

| Example | R | $R_1$ | $R_2$ | $R_3$ | $R_4$ | Yield (%) | Salts | Melting point ° C. |
|---|---|---|---|---|---|---|---|---|
| 71 | H | Ph-3,4,5-triOMe | Me | $CO_2H$ | $NH_2$ | 77 | Na, 1.6$H_2O$ | 311 |
| 72 | H | Ph-2,3,4-triOMe | Me | $CO_2H$ | $NH_2$ | 85 | Na, 2$H_2O$ | 279 |
| 73 | H | 3-thienyl | Me | OMe | $NH_2$ | 81 | HCl, 0.2 $H_2O$ | 212 |
| 74 | H | 3-furyl | Me | OMe | $NH_2$ | 95 | HCl, 1$H_2O$ | dec. 216 |
| 75 | H | 2-thienyl | Me | OMe | $NH_2$ | 85 | 0.7HCl, 0.1$H_2O$ | 219 |
| 76 | 6-CONHMe | Ph-4-OMe | Me | OMe | $NH_2$ | 41 | HCl, 1.8$H_2O$ | dec. 238 |
| 77 | 6-$NH_2$ | Ph-4-OMe | Me | OMe | $NH_2$ | 60 | 2HCl, 0.25 $H_2O$ | 187 |

Example 78

Methyl [3-(4-amino-3-methoxybenzoyl)-6-hydroxy-2-methylindolizin-1-yl]carboxylate 100 mg of Pd/C (10%) are added to 1.0 g (2.17 mmol) of methyl [6-(benzyloxy)-3-(3-methoxy-4-nitrobenzoyl)-2-methylindolizin-1-yl]carboxylate in suspension in 30 mL of dimethylformamide and 30 mL of tetrahydrofuran. The reaction mixture is stirred at 10 bar of hydrogen for 48 hours.

Ultrafiltration is performed (Millipore™ filter 5 µM) and the catalyst is washed with dimethylformamide.

The filtrate is concentrated under reduced pressure to give 780 mg of a yellow solid.
Yield: 91%
Melting point: 184° C.

Example 79

[3-(4-amino-3-methoxybenzoyl)-6-hydroxy-2-methylindolizin-1-yl]carboxylic Acid

This compound is obtained according to the same method as the compound of Example 78 above by debenzylation of the hydroxyl functional group and reduction of the nitro functional group, by catalytic hydrogenation under pressure of the compound of Example 97.

A yellow solid is obtained which is salified in the form of a sodium salt.

A yellow solid is obtained (Na salt, 1.5$H_2O$)
Yield: 70%
Melting point: 214° C.

Example 80

[3-(4-amino-3-methoxybenzoyl)-8-{2-(dimethylamino)ethoxy}-2-methylindolizin-1-yl]carboxylic Acid This compound is obtained according to the same method as the compound of Example 78 above, by reducing the nitro functional group, by catalytic hydrogenation under pressure of the compound of Example 98.

A yellow solid is obtained which is salified in the form of a lithium salt hydrate (2.3H$_2$O).

Yield: 76%
Melting point: 178° C.

Example 81

Methyl [3-(4-amino-3-methoxybenzoyl)-6-methoxy-2-methylindolizin-1-yl]carboxylate 503 mg (1.54 mmol) of cesium carbonate and 123 μL (1.29 mmol) of dimethyl sulfate are added to 460 mg (1.29 mmol) of methyl [3-(4-amino-3-methoxybenzoyl)-6-hydroxy-2-methylindolizin-1-yl]carboxylate in suspension in 20 mL of acetone.

The reaction mixture is stirred at room temperature for 30 minutes and then poured over water and extracted with ethyl acetate.

The organic phase is washed with a saturated aqueous sodium chloride solution, dried over sodium sulfate and then concentrated under reduced pressure.

The product is purified by chromatography on a silica gel, eluting with a mixture of dichloromethane and methanol (100/0 to 98/2).

470 mg of a yellow solid are obtained.
Yield: 98%

Example 82

Methyl [3-(4-amino-3-methoxybenzoyl)-6-(2-ethoxy-2-oxoethoxy)-2-methylindolizin-1-yl]carboxylate This compound is obtained by carrying out the procedure according to the preparation described in the example above, by alkylating methyl [3-(4-amino-3-methoxybenzoyl)-6-hydroxy-2-methylindolizin-1-yl]carboxylate with ethyl bromoacetate.

A yellow powder is obtained.
Yield: 84%
Melting point: 192° C.

Example 83

[7-(acetylamino)-3-(4-amino-3-methoxybenzoyl)-2-methylindolizin-1-yl]carboxylic Acid 450 mg of Pd/C (10%) are added to 855 mg (1.76 mmol) of benzyl [7-(acetylamino)-3-(3-methoxy-4-nitrobenzoyl)-2-methylindolizin-1-yl]carboxylate in suspension in 9 mL of dimethylformamide.

The reaction mixture is stirred at 10 bar of hydrogen for 5 hours.

The medium is filtered on a silica bed, eluting with a mixture of dichloromethane and methanol (9-1) and then the filtrate is concentrated in order to obtain a yellow solid which is taken up in ethanol, then filtered and dried.

561 mg of a yellow powder are obtained which are suspended in 6 mL of methanol and then 1.40 mL of 1 N sodium hydroxide (1 equivalent) are added.

The solution is concentrated under reduced pressure and the solid obtained is washed with acetone.

After drying, 596 mg of a green solid are obtained (Na salt, 3.7H$_2$O).

Yield: 84%
Melting point: 288-291° C. (decomposition)

Example 84 to 88

By carrying out the procedure according to the procedure described above, the compounds described in Table VIII below are synthesized by hydrogenation under pressure of the benzyl ester of R$_1$ and reducing the nitro of R$_3$ or R$_4$.

TABLE IV

| Example | R | R$_1$ | R$_2$ | R$_3$ | R$_4$ | Yield % | Salt | Melting point ° C. |
|---|---|---|---|---|---|---|---|---|
| 84 | 7-NH$_2$ | CO$_2$H | Me | OMe | NH$_2$ | 84% | Na, 1.0 H$_2$O | 255-259 |
| 85 | 7-NHCO$_2$Et | CO$_2$H | Me | OMe | NH$_2$ | 83% | Na, 2.05 H$_2$O | 257 |
| 86 | 7-NHSO$_2$Me | CO$_2$H | Me | OMe | NH$_2$ | 88% | Na, 2.35 H$_2$O | 207-213 |
| 87 | 7-NHMe | CO$_2$H | Me | OMe | NH$_2$ | 42% | Na, 2.0 H$_2$O | 209-219 |
| 88 | 7-NMe$_2$ | CO$_2$H | Me | OMe | NH$_2$ | 83% | Na, 3.2 H$_2$O | 222-227 |

Example 89

2-{[3-(4-amino-3-methoxybenzoyl)-1-(methoxycarbonyl)-2-methyl-indolizin-6-yl]-oxy}acetic Acid 272 mg (6.81 mmol) of sodium hydroxide pellets are added to 600 mg (1.36 mmol) of methyl [3-(4-amino-3-methoxybenzoyl)-6-(2-ethoxy-2-oxoethoxy)-2-methylindolizin-1-yl]oxy}acetate in solution in 20 mL of dioxane and the medium is heated under reflux for 1 hour. The reaction medium is concentrated under reduced pressure. The residue is taken up in water and the solution obtained is acidified to pH 3-4 with a 10% aqueous potassium hydrogen sulfate solution and then extracted with ethyl acetate.

The organic phase is separated by decantation, washed with a saturated aqueous sodium chloride solution, dried over sodium sulfate and concentrated under reduced pressure.

The 398 mg of yellow solid obtained are then salified in the form of a sodium salt.

A yellow solid is obtained (Na salt, 1.5H$_2$O)
Yield: 68%
Melting point: 182° C.

Example 90

[3-(4-Amino-3-methoxybenzoyl)-1-methoxy-2-methylindolizin-6-yl]carboxylic Acid 2.01 mL (2.01 mmol) of 1N sodium hydroxide are added to 225 mg (0.61 mmol) of methyl [3-(4-amino-3-methoxybenzoyl)-1-methoxy-2-methylindolizin-6-yl]carboxylate in a mixture of 20 mL of methanol-dioxane (1-1) and the medium is heated at 50° C. for 6 hours.

The reaction medium is concentrated under vacuum and the residue is taken up in water and ethyl acetate. The aqueous phase is separated by decantation, washed with ethyl acetate and then acidified with 2 mL of 1N hydrochloric acid.

The precipitate formed is filtered, washed with water and then dried.

189 mg of an orange-coloured solid obtained are then salified in the form of a sodium salt.

An orange-coloured solid (Na salt) is obtained
Yield: 87%
Melting point: 290° C.

Example 91

[3-(4-amino-3-methoxybenzoyl)-6-(benzyloxy)-2-methylindolizin-1-yl]carboxylic Acid 358 mg (8.95 mmol) of sodium hydroxide pellets are added to 800 mg (1.79 mmol) of methyl [3-(4-amino-3-methoxybenzoyl)-6-(benzyloxy)-2-methylindolizin-1-yl]carboxylate in solution in 30 mL of dioxane and 10 mL of methanol and the medium is heated under reflux for 16 hours.

The reaction medium is concentrated under reduced pressure. The residue is taken up in water and the solution obtained is acified to pH 5 with a 10% aqueous potassium hydrogen sulfate solution.

The precipitate formed is filtered, washed with water and then dried. The 760 mg of yellow solid obtained are then salified in the form of a sodium salt.

A yellow solid is obtained (Na salt)
Yield: 98%
Melting point: 258° C.

Examples 92 and 93

By carrying out the procedure according to the procedure described above, the compounds of formula Ij described in Table IX below are synthesized by saponification of the ester functional group contained in the substituent R$_1$ of the compounds of formula Ib with sodium hydroxide.

Example 94

[3-(4-amino-3-methoxybenzoyl)-6-(carbomethoxy)-2-methylindolizin-1-yl]carboxylic Acid 1.81 g (45.40 mmol) of sodium hydroxide pellets are added to 800 mg (1.81 mmol) of methyl [3-(4-amino-3-methoxybenzoyl)-6-(2-ethoxy-2-oxoethoxy)-2-methylindolizin-1-yl]carboxylate in solution in 40 mL of dioxane and 20 mL of methanol and the medium is heated under reflux for 72 hours. The reaction medium is cooled and then acidified to pH 5 with a 10% aqueous potassium hydrogen sulfate solution. The precipitate formed is filtered, washed with water and then dried. The 390 mg of yellow solid obtained are then salified in the form of a sodium salt.

A yellow solid is obtained (diNa salt, 4H$_2$O)
Yield: 54%
Melting point: 273° C.

Example 95

[3-(4-amino-3-methoxybenzoyl)-8-(carbomethoxy)-2-methylindolizin-1-yl]carboxylic Acid This compound is obtained by carrying out the procedure according to the preparation described in Example 94 above by saponification of the 2 ester functional groups of the compound methyl [3-(4-amino-3-methoxybenzoyl)-8-(2-ethoxy-2-oxoethoxy)-2-methylindolizin-1-yl]carboxylate with sodium hydroxide.

A yellow powder is obtained after salification (diNa salt, 3H$_2$O)
Yield: 45%
Melting point: 268° C.

Example 96

[3-(4-amino-3-methoxybenzoyl)-6-(methoxy)-2-methylindolizin-1-yl]carboxylic Acid 48 mg (11.4 mmol) of lithium hydroxide are added to 420 mg (1.14 mmol) of methyl [3-(4-amino-3-methoxybenzoyl)-6-(methoxy)-2-methylindolizin-1-yl]carboxylate dissolved in 12 mL of dioxane.

The reaction mixture is heated at 70° C. for 13 hours and then cooled to room temperature, poured into water and extracted with ethyl acetate. The aqueous solution is acidified

TABLE IX

| Example | R | R$_1$ | R$_2$ | R$_3$ | R$_4$ | Yield % | Salt | Melting point ° C. |
|---|---|---|---|---|---|---|---|---|
| 92 | 7-Me | CO$_2$H | Me | OMe | NH$_2$ | 89 | Na, 1.35 H$_2$O | 295 |
| 93 | 8-OMe | CO$_2$H | Me | OMe | NH$_2$ | 91 | Na, 0.9 H$_2$O | 201 | to pH 5 by adding a 10% aqueous sodium hydrogen sulfate solution. The medium is extracted with ethyl acetate. The organic phase is washed with a saturated sodium chloride solution, it is dried on sodium sulfate and then it is concentrated under reduced pressure. The 232 mg of yellow solid are then salified in the form of a sodium salt, $1.5H_2O$ Yield: 80%

Melting point: 242° C.

Examples 97 and 98

By carrying out the procedure according to the procedure described above, the compounds of formula Ij described in Table X below are synthesized by saponification of the ester functional group contained in the substituent $R_1$ of the compounds of formula Ia with sodium hydroxide.

TABLE X

| Example | R | $R_1$ | $R_2$ | $R_3$ | $R_4$ | Yield % | Melting point ° C. |
|---|---|---|---|---|---|---|---|
| 97 | 6-OBn | $CO_2H$ | Me | OMe | $NO_2$ | 89% | 193 |
| 98 | 8-O(CH$_2$)$_2$NMe$_2$ | $CO_2H$ | Me | OMe | $NO_2$ | 91% | 198 |

Example 99

2-amino-5-({1-methoxy-2-methyl-6-[(methylamino) carbonyl]indolizin-3-yl}-carbonyl)benzoic Acid 3.03 mL of a 1 N sodium hydroxide solution are added to 710 mg (1.44 mmol) of methyl 5-({1-methoxy-2-methyl-6-[(methylamino)carbonyl]indolizin-3-yl}carbonyl)-2-[2,2,2-trifluoroacetyl)amino]benzoate in solution in 12 mL of dioxane. The reaction medium is heated at 60° C. for 16 hours and then it is allowed to return to room temperature and concentrated under reduced pressure. The residue is taken up in water and washed with ethyl ether. After decantation, the aqueous phase is acidified with a molar hydrochloric acid solution and extracted with ethyl acetate. The organic phase is separated by decantation, washed with water, dried over sodium sulfate and concentrated under reduced pressure. The 400 mg of yellow solid are then salified in the form of a sodium salt dihydrate ($2H_2O$).

Yield: 73%

Melting point: 311° C.

Examples 100 and 101

By carrying the procedure according to the procedure described above, the compounds of formula Ie described in Table XI below are synthesized by basic hydrolysis of the ester functional group and deprotection of the amino functional group contained in the substituent $R_3$ and/or $R_4$ of the compounds of formula Ic with sodium hydroxide.

TABLE XI

| Example | R | $R_1$ | $R_2$ | $R_3$ | $R_4$ | Yield % | Salt | Melting point ° C. |
|---|---|---|---|---|---|---|---|---|
| 100 | 6-CONMe$_2$ | OMe | Me | $CO_2H$ | $NH_2$ | 80 | Na, $3H_2O$ | 288 |
| 101 | 6-OMe | OMe | Me | $CO_2H$ | $NH_2$ | 31 | Na, $4.4H_2O$ | 318 |

Example 102

2-Amino-5-{[2-methyl-1-(2-thienyl)indolizin-3-yl]carbonyl}benzoic Acid 2.34 mL (2.34 mmol) of 1N sodium hydroxide are added to 0.29 g (0.74 mmol) of methyl 2-amino-5-{[2-methyl-1-(2-thienyl)indolizin-3-yl]carbonyl}benzoate in a mixture of 16 mL of dioxane-methanol (1-1) and the medium is heated at 70° C. for 6 hours. The reaction medium is evaporated to dryness. The residue is taken up in 1N hydrochloric acid and extracted with ethyl acetate. The organic phase is washed with water, dried over sodium sulfate and evaporated under reduced pressure. The product is purified by flash chromatography on silica gel, eluting with a dichloromethane-methanol (98-2) mixture. The 280 mg of yellow solid obtained are then salified in the form of a sodium salt, $1.25H_2O$.

Yield: quantitative

Melting point: 294° C.

Examples 103 to 109

By carrying out the procedure according to the protocol described above, the compounds of formula Ie described in Table XII below are synthesized by saponification of the ester functional group contained in the substituents $R_3$ or $R_4$ of the compounds of formula Ib and optionally of the ester functional group of the substituent R with 1N sodium hydroxide.

TABLE XII

| Example | R | $R_1$ | $R_2$ | $R_3$ | $R_4$ | Yield % | Salt | Melting point ° C. |
|---|---|---|---|---|---|---|---|---|
| 103 | H | 3-thienyl | Me | $CO_2H$ | $NH_2$ | 61 | Na, $1.5H_2O$ | 304 |
| 104 | H | Ph-4-OMe | Me | $CO_2H$ | $NH_2$ | 95 | Na, $2.5H_2O$ | 298 |

TABLE XII-continued

| Example | R | $R_1$ | $R_2$ | $R_3$ | $R_4$ | Yield % | Salt | Melting point ° C. |
|---|---|---|---|---|---|---|---|---|
| 105 | 6-CONH$_2$ | Ph-4-OMe | Me | CO$_2$H | NH$_2$ | 75 | Na, 1.9H$_2$O | 283 |
| 106 | H | Ph-3-OMe | Me | CO$_2$H | NO$_2$ | 98 | — | 128 |
| 107 | H | Ph-3,4,5-triOMe | Me | CO$_2$H | NO$_2$ | 98 | — | 253 |
| 108 | H | Ph-2,3,4-OMe | Me | CO$_2$H | NO$_2$ | 99 | — | 116 |
| 109 | 6-CO$_2$H | Ph-4-OMe | Me | CO$_2$H | NH$_2$ | 44 | 2Na | 355 |

Example 110

2-amino-5-[(1-methoxy-2-methylindolizin-3-yl)carbonyl]benzamide 702.4 mg (15.9 mmol) of benzotriazol-1-yloxy-tris(dimethylamino)phosphonium hexafluorophosphate (BOP) are added to 500 mg (14.4 mmol) of sodium 2-amino-5-[(1-methoxy-2-methylindolizin-3-yl)carbonyl]benzoate in 8 mL of dimethylformamide and the medium is stirred for one hour at room temperature and then a stream of ammonia is bubbled through the reaction medium for 5 minutes and the medium is kept stirring at room temperature overnight.

Water is added and the medium is extracted with ethyl acetate. The organic phase is washed with a saturated aqueous sodium chloride solution, dried over sodium sulfate and concentrated under reduced pressure. The product is purified by flash chromatography on a silica gel, eluting with a mixture of dichloromethane and methanol (99-1 and then 98-2).

After evaporation, the product is crystallized from ethyl ether. 310 mg of a yellow powder are obtained.

Yield: 67%

Melting point: 156° C.

Example 111

2-amino-N-hydroxy-5-[(1-methoxy-2-methylindolizin-3-yl)carbonyl]benzamide

This compound is obtained by carrying out the procedure according to the preparation described in Example 110 above, by coupling hydroxylamine to the acid functional group of the compound sodium 2-amino-5-[(1-methoxy-2-methylindolizin-3-yl)carbonyl]benzoate after its activation with BOP.

A yellow powder is obtained.

Yield: 71%

Melting point: 205° C.

Example 112

Study of the Binding of $^{125}$I-b-FGF to the Purified Receptor FGF R α IIIc by the Proximity Scintillation Method NBS plates (NBS plate 96 well solid white CORNING 3600) are coated with 100 µl of 0.1% gelatine per well, for 2 hours at 37° C.

At the end of the incubation, the coating is removed, the plates are rinsed and thoroughly dried. 100 µl of binding buffer (40 mM Bis Tris buffer, pH 7.0) are distributed into the plates.

Dilutions of the compounds of the invention are distributed into the wells in an amount of 10 µl/well. There are then distributed 10 µl/well of b-FGF (AMERSHAM ARM 35050) and 10 µl/well of FGF R α IIIc (R&D Systems 658 FR). Next, there are added 10 µl/well of $^{125}$I-b-FGF (Dupont NEN NEX 268—specific activity>70 µCi) and 50 µl/well of SPA beads (AMERSHAM RPQN 00019). The plate is shaken for a few seconds and it is incubated for 60 minutes at 37° C., protected from light.

At the end of the incubation, the plate is read in a MIBROBETA TRILUX radioactivity counter (WALLAC-PERKINELMER)

The compounds of the invention demonstrated a specific activity of between $10^{-6}$ M and $10^{-9}$ M.

Example 113

Effects of the Compounds of Formula I on the Proliferation of IUVECs Versus 30 ng/mL of b-FGF or 10 ng/mL of a-FGF Coat the 24-well plates (FALCON PRIMARIA) with 200 µl of a solution of fibronectin (50 µg/mL prepared in PBS)/well.

Inoculate in an amount of 30 000 cells/mL/well in an RPMI 1640 medium+10% FCS+1% glutamine+heparin-ECGF (HE) mixture.

Incubate at 37° C., 5% CO$_2$, the time required for the cells to adhere.

Dissolve the products and prepare solutions in DMSO/reaction medium having a final concentration of 1 µM final at $10^{-7}$ M.

After adhesion of the cells for 6 hours at 37° C. in the presence of 5% CO$_2$, the medium is replaced with RPMI 1640 0.1% FSC+glutamine+HE.

For the derivatization, there is used as negative control 0.1% FCS, as positive control 0% FCS and as control 0.1% FCS+30 ng/mL of b-FGF or 10 ng/mL of a-FGF. Incubation is then carried out for 24 hours at 37° C. in the presence of 5% CO$_2$.

The second day, the cells are rinsed with 1 mL PBS and 200 µl of trypsin, and they are then recovered in isotone. Counting is carried out (n>9 µm).

In this test of proliferation of endothelial cells induced by b-FGF or a-FGF, the compounds of the invention demonstrated a specific activity of between $10^{-5}$ M and $10^{-9}$ M.

Example 114

Model of Angiogenesis In Vitro

Prepare the gels by distributing into each chamberslide well (Biocoat Cellware rat tail collagen, Type I, 8-well culture sides: Becton Dickinson 354630) 160 µl of matrigel diluted ⅙ (Growth factor reduced Matrigel: Becton Dickinson 356230) in collagen (Rat Tail Collagen, type I: Becton Dickinson 354236). Allow to gel for 1 hour at 37° C.

Inoculate the human vein endothelial cells (HUVEC ref: C-015-10C -cascade Biologics, INC) or porcine arterial endothelial cells (PAEC) at $15 \cdot 10^3$ cells/well in 400 µl of EBM medium (Clonetics C3121)+2% FBS+hEGF 10 µg/mL for the HUVECs and DMEM+3% FCS+2 mM glutamine+1 mM sodium pyruvate+1% nonessential amino acids (GIBCO) for the PAECs.

Stimulate with b-FGF (TEBU/Peprotech) 10 ng/mL or a-FGF (TEBU/Peprotech) 10 ng/mL in the presence or otherwise of the products of the invention for 24 h at 37° C. in the presence of 5% $CO_2$.

After 24 hours, fix the cells and stain the slide with the Masson trichrome before examination under the microscope X4 lens and image analysis (BIOCOM—Visiolab 2000 software).

For the test of angiogenesis in vitro induced by b-FGF or a-FGF, the compounds of the invention demonstrated a specific activity of between $10^{-7}$ M and $10^{-11}$ M.

Example 115

Model of Inflammatory Angiogenesis in Mice

Angiogenesis is required for the development of chronic inflammatory diseases such as rheumatoid arthritis, IBD, but also for the development of solid tumours. The formation of new vessels not only allows the perfusion of pathological tissues, but also the transport of cytokines responsible for establishing the chronicity of the disease.

The model described by Colville-Nash P. et al., (*D. JPET.*, 1995, Vol. 274 No. 3, pp. 1463-1472) makes it possible to study pharmacological agents capable of modulating the appearance of angiogenesis.

The animals, nonconsanguineous white mice of about 25 g, are anaesthetized with sodium pentobarbital (60 mg/kg; Sanofi Nutrition Santé Animale) by the intraperitoneal route.

An air pouch is created on the back of the mice by injecting 3 mL of air subcutaneously.

After becoming conscious, the animals receive a treatment, in general by force-feeding, and receive an injection of 0.5 mL of Freund's adjuvant (Sigma) with 0.1% croton oil (Sigma) in the pouch.

Seven days later, the mice are again anaesthetized and placed on a heating plate at 40° C. One mL of carmine red (5% in 10% gelatine—Aldrich Chemicals) is injected into the tail vein. The animals are then placed at 4° C. for 2-3 hours.

The skins are then removed and dried for 48 hours in an oven at 56° C. The dry tissues are weighed and placed in 1.8 mL of digestion buffer (2 mM dithiothreitol, 20 mM $Na_2HPO_4$, 1 mM EDTA, 12 U/mL papain) for 24 hours.

The stain is then dissolved in 0.2 mL of 5 M NaOH. The skins are centrifuged at 2000 g for 10 min. The supernatants are filtered on 0.2 µm cellulose acetate membranes. The filtrates are read in a spectrophotometer at 492 nm against a carmine red calibration series.

Two parameters are studied: the dry weight of the granuloma and the quantity of stain after digestion of the tissues.

The results are expressed as mean values (±SEM). The differences between the groups are tested with an ANOVA followed by Dunnet's test for which the reference group is the "solvent control" group.

The compounds of the invention are active by the oral route at doses of 0.1 to 100 mg/kg.

Example 116

Model of MATRIGEL Angiogenesis in Mice

The model described by Passaniti et al. (*Laboratory Investigation* (1992) 67 (4) pp. 519-524) makes it possible to study pharmacological agents capable of modulating the appearance of angiogenesis which is specifically induced by b-FGF. FGF2 (Peprotech) is added to Matrigel (Beckton Dickinson) kept in liquid form at 4° C., in an amount of 300 ng/mL. After homogenization, the mixture (0.5 mL) is subcutaneously injected into the base of the back of black female mice (C57/B16) of about 20 g, anaesthetized beforehand with sodium pentobarbital (60 mg/kg; Sanofi Nutrition Santé Animale) by the intraperitoneal route. The animals are treated by force-feeding. After 5 days, the mice are again anaesthetized and the skin of the base of the back is removed; at this stage, the qualitative differences in vascularization of the granuloma are evaluated (awarded scores) and the granulomas are photographed. An assay of DNA in the granulomas is then carried out in order to quantify its cellularity. For that, the isolated granulomas are digested with collagenase (3 mg/mL) overnight at 37° C. After centrifugation at 850 g for 10 min, the supernatant is discarded and the pellet is redissolved in 1.2 mL of PBS buffer containing 1 mM $CaCl_2$, 1 mM $MgCl_2$ and 5 mM glucose. The quantity of DNA present is measured with the aid of a kit (Cyquant-GR®, Molecular probe) according to the instructions of the supplier.

The results are expressed as mean values (±SEM). The differences between the groups are tested with an ANOVA followed by a Dunnet's test for which the reference group is the "solvent control" group.

For the histological studies, the granulomas are removed with the muscle and the skin, fixed overnight in a 10% formaldehyde solution and embedded in paraffin (Embedder Leica®). The granulomas are then sliced with the aid of a microtome (Leica) and stained with the Masson's trichrome stain. Neovascularization of the granulomas is then evaluated. The vascularization levels are between a value of 0 and 5.

The compounds of the invention are active by the oral route at doses of 0.1 to 100 mg/kg.

Example 117

Model of Tumour Angiogenesis in Mice

This model makes it possible to study pharmacological agents capable of modulating the appearance of angiogenesis specifically induced by tumour development. C56/B16 mice of about 20 g are anaesthetized with sodium pentobarbital (60 mg/kg; Sanofi Nutrition Santé Animale) by the intraperitoneal route. The tumours are established by subcutaneous injection on the back of mouse Lewis Lung cells in an amount of $2 \cdot 10^5$ cells/mouse.

After 5 days, the mice are treated daily by force-feeding. The size of the tumours is measured twice per week for 21 days and the tumour volume is calculated using the formula: $[\pi/6(\omega_1 \times \omega_2 \times \omega_2)]$, where oat represents the largest diameter and $\omega_2$ represents the smallest diameter.

The results are expressed as mean values (±SEM). The differences between the groups are tested with an ANOVA followed by a Dunnet's test for which the reference group is the "solvent control" group.

The compounds of the invention are active by the oral route at doses of 0.1 to 100 mg/kg.

Example 118

Effect on Thrombopenia

Thrombopenia remains a pathology for which there are few effective treatments apart from the transfusion of platelet concentrates and thrombopoietin (Kaushansky, K. *New Eng J Med* (1998), 339, pp 746-754).

Anticancer chemotherapy constitutes one of the major causes of thrombopenia. One of the agents for chemotherapy, carboplatin, has been widely used to induce thrombopenia in mice and to thus be able to characterize the effect of compounds capable of improving the platelet level such as for example thrombopoietin (Hokom M M et al., *Blood* (1995), 86, pp 4486-4492).

150 mg/kg of carboplatin were administered intraperitoneally to balbC mice weighing 20 g. A blood sample was collected periodically by retro-orbital puncture and the circulating platelet level is determined by a haematology automated machine (MS9™ from Melet-Schloesing Laboratoires, Cergy-Pontoise, France). Under these conditions, a reversible thrombopenia is observed with a nadir situated 9 to 10 days after the administration of carboplatin (reduction in the circulating platelet level by 50-60%).

The compounds according to the invention or their solvent (a blank—control) are administered orally for 5 days by starting the treatment 7 days before the administration of carboplatin. The experiments were carried out on groups comprising 10-12 mice and the results are expressed as a mean±standard error. Under these conditions, the compounds of the invention increase the circulating platelet level at doses of 0.1 to 100 mg/kg.

Example 119

Model of CNV (Choroidal Neovascularization) Induced by Argon Laser in Mice

A major feature of the loss of ocular transparency is the neovascularization and the resulting haemorrhages which cause considerable functional disorders in the eye and which result in early blindness. Recently, the study of the mechanisms involved in the phenomena of ocular neovascularization has made it possible to demonstrate the involvement of proangiogenic factors in these pathologies.

The model of laser induced choroidal neoangiogenesis described by Rakic J M et al. in *Invest Ophthalmol Vis Sci.* (2003) *July;* 44(7), pp 3186-3193 makes it possible to study pharmacological agents capable of modulating neovascularization of the choroid.

The mice are anaesthetized by intraperitoneal injection of Avertin™. The two pupils are dilated with a 1% tropicamide solution by topical application, and three lesions are made around the optical disc with the aid of an argon laser (532 nm; "spot size" diameter 50 μm; duration 0.05 sec; 400 mW). The optical disc is then covered with a lens.

14 days later, the mice are sacrificed and the eyes enucleated and fixed in a buffer containing 3.5% of Formalin™, wrapped in tissue TeK™ (Miles Laboratories, Naperville, Ill.) and frozen in liquid nitrogen so as to be able to produce sections with the aid of a cryostat.

The quantification of choroidal neovascularization was carried out by a quantitative morphometric study which makes it possible to evaluate the thickness of the network of neovessels present in the choroid, with the aid of a computer-aided image analyzing system (Olympus Micro Image version 3.0 for Windows 95/NT, Olympus Optical CO. Europe GmBH).

Neovascularization is estimated by the ratio (B/C) of the thickness of the pigmented layer of the choroid at the level of the lesion (B) to the thickness of this same pigmented layer in a region adjacent to the lesion (C). The results are expressed as mean values (±sem). The differences between the treated groups and the control groups are tested with an ANOVA followed by a Dunnet test in which the reference group is the "control solvent" group.

The compounds of the invention are active orally at doses of 0.1 to 100 mg/kg.

We claim:
1. A compound of formula I:

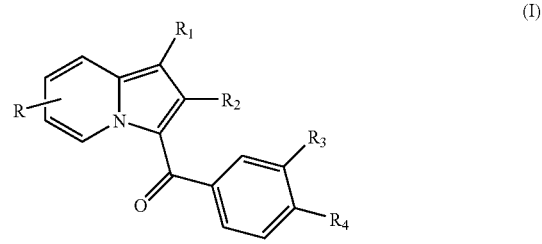

wherein:
R at 6-, 7- or 8-position of the indolizine ring is hydrogen, halogen, methyl, hydroxy, $(C_1-C_5)$-alkoxy, carboxy, $(C_2-C_6)$-alkoxycarbonyl, —$NR_5R_6$, —NH—$SO_2$-Alk, —NH—CO-Alk, —NH—$CO_2$-Alk, —O-Alk-$COOR_7$, —O-Alk-$NR_5R_6$, —O—$(CH_2)_n$—Ph, or —CO—$NR_5R_6$;

$R_1$ is $(C_1-C_5)$-alkoxy, carboxy, $(C_2-C_6)$-alkoxycarbonyl, or Ph;

$R_2$ is $(C_1-C_5)$-alkyl, $(C_3-C_6)$-cycloalkyl, or phenyl, wherein the phenyl is optionally substituted with one or more halogen, or $(C_1-C_5)$-alkoxy;

$R_3$ and $R_4$ independently are hydroxy, $(C_1-C_5)$-alkoxy, amino, carboxy, $(C_2-C_6)$-alkoxycarbonyl, nitro, —$NR_5R_6$, —NH—CO-Alk, —NH—CO—$CF_3$, —CO—$NR_5R_6$, or —CO—NHOH;

Alk is $(C_1-C_5)$-alkyl or $(C_1-C_5)$-alkylene;

n is an integer from 0 to 5;

$R_5$ and $R_6$ independently are hydrogen, $(C_1-C_5)$-alkyl, or benzyl;

$R_7$ is hydrogen or $(C_1-C_5)$-alkyl; and

Ph is phenyl optionally substituted with one or more halogen, $(C_1-C_5)$-alkoxy, carboxy, or $(C_2-C_6)$-alkoxycarbonyl;

provided that when R is hydrogen, and $R_3$ and $R_4$ independently are not —CO—$NR_5R_6$ or —CO—NHOH, then $R_1$ is not $(C_1-C_5)$-alkoxy, carboxy, or $(C_2-C_6)$-alkoxycarbonyl;

or a pharmaceutically acceptable salt thereof.

2. The compound according to claim 1, wherein:
R at 6-, 7- or 8-position of the indolizine ring is hydrogen, halogen, hydroxy, $(C_1-C_5)$-alkoxy, carboxy, $(C_2-C_6)$-alkoxycarbonyl, —$NR_5R_6$, —NH—$SO_2$-Alk, —NH—CO-Alk, —NH—$CO_2$-Alk, —O-Alk-$COOR_7$, —O-Alk-$NR_5R_6$, or —CO—$NR_5R_6$;

$R_1$ is $(C_1-C_5)$-alkoxy, carboxy, $(C_2-C_6)$-alkoxycarbonyl, or Ph; and

R₃ and R₄ independently are hydroxy, $(C_1-C_5)$-alkoxy, amino, carboxy, $(C_2-C_6)$-alkoxycarbonyl, nitro, —NR₅R₆, —NH—CO-Alk, —CO—NR₅R₆, or —CO—NHOH;

or a pharmaceutically acceptable salt thereof.

3. The compound according to claim 1, wherein:

R at 6-, 7- or 8-position of the indolizine ring is hydrogen, halogen, hydroxy, $(C_1-C_5)$-alkoxy, $(C_2-C_6)$-alkoxycarbonyl, —NR₅R₆, or —CO—NR₅R₆;

R₁ is $(C_1-C_5)$-alkoxy, carboxy or Ph;

R₂ is $(C_1-C_5)$-alkyl; and

R₃ and R₄ independently are hydroxy, $(C_1-C_5)$-alkoxy, amino, carboxy, or —NR₅R₆;

or a pharmaceutically acceptable salt thereof.

4. The compound according to claim 1, which is [3-(4-amino-3-methoxybenzoyl)-6-methoxy-2-methylindolizin-1-yl]carboxylic acid, (4-amino-3-methoxyphenyl) [1-(4-methoxyphenyl)-2-methylindolizin-3-yl]methanone, 3-(4-amino-3-methoxybenzoyl)-(1-methoxy-N,2-dimethylindolizin-6-yl)carboxamide, [3-(4-amino-3-methoxybenzoyl)-2-methyl-7-(methylamino)indolizin-1-yl]carboxylic acid, [3-(4-amino-3-methoxybenzoyl)-7-(dimethylamino)-2-methylindolizin-1-yl]carboxylic acid, 2-amino-5-({1-methoxy-2-methyl-6-[(methylamino)carbonyl]indolizin-3-yl}-carbonyl)benzoic acid, 2-amino-5-[(1,6-dimethoxy-2-methylindolizin-3-yl)carbonyl]benzoic acid, 2-amino-5-[(1-methoxy-2-methylindolizin-3-yl)carbonyl]benzamide, or [3-(4-amino-3-methoxybenzoyl)-1-(4-methoxyphenyl)-2-methylindolizin-6-yl]carboxamide, or a pharmaceutically acceptable salt thereof.

5. A pharmaceutical composition comprising the compound according to claim 1 or a pharmaceutically acceptable salt thereof and an inert excipient.

6. A pharmaceutical composition comprising the compound according to claim 2 or a pharmaceutically acceptable salt thereof and an inert excipient.

7. A pharmaceutical composition comprising the compound according to claim 3 or a pharmaceutically acceptable salt thereof and an inert excipient.

8. A pharmaceutical composition comprising the compound according to claim 4 or a pharmaceutically acceptable salt thereof and an inert excipient.

9. A method for treating carcinoma having a high degree of vascularisation, in a patient in need thereof comprising administering to the patient a pharmaceutically effective amount of the compound according to claim 1 or a pharmaceutically acceptable salt thereof, wherein the carcinoma having a high degree of vascularisation is carcinoma of lung, breast, prostate or oesophagus.

10. A method for treating cancer that induces metastasis, in a patient in need thereof comprising administering to the patient a pharmaceutically effective amount of the compound according to claim 1 or a pharmaceutically acceptable salt thereof wherein the cancer that induces metastasis is colon cancer, stomach cancer, melanoma, glioma, lymphoma or leukaemia.

* * * * *

UNITED STATES PATENT AND TRADEMARK OFFICE
CERTIFICATE OF CORRECTION

PATENT NO. : 7,553,845 B2  
APPLICATION NO. : 11/378972  
DATED : June 30, 2009  
INVENTOR(S) : Chantal Alcouffe et al.

Page 1 of 1

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 105 days.

should read (*) Notice: Subject to any disclaimer, the term of this patent is extended or adjusted under 35 U.S.C. 154(b) by 210 days.

Signed and Sealed this

Thirteenth Day of April, 2010

David J. Kappos  
*Director of the United States Patent and Trademark Office*

UNITED STATES PATENT AND TRADEMARK OFFICE
CERTIFICATE OF CORRECTION

PATENT NO. : 7,553,845 B2  Page 1 of 1
APPLICATION NO. : 11/378972
DATED : June 30, 2009
INVENTOR(S) : Chantal Alcouffe et al.

It is certified that error appears in the above-identified patent and that said Letters Patent is hereby corrected as shown below:

In column 10, line 5, delete " 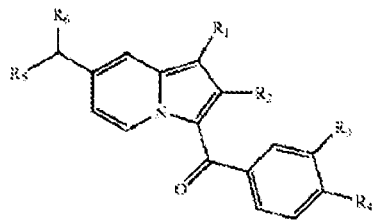 " and insert -- 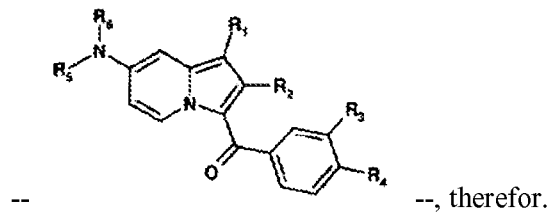 --, therefor.

In column 22, line 37, delete "dimethynicotinamide" and insert -- dimethylnicotinamide --, therefor.

In column 37, line 55, below "Yield: 98%" insert -- Melting point: 95° C. --, therefor.

In column 44, line 29, delete "IUVECs" and insert -- HUVECs --, therefor.

In column 46, line 62, delete "oat" and insert -- $\omega_1$ --, therefor.

Signed and Sealed this
Twenty-sixth Day of April, 2011

David J. Kappos
*Director of the United States Patent and Trademark Office*